United States Patent
Stelzle et al.

(10) Patent No.: US 8,268,152 B2
(45) Date of Patent: Sep. 18, 2012

(54) MICROFLUIDIC SYSTEM AND METHOD FOR ASSEMBLING AND FOR SUBSEQUENTLY CULTIVATING, AND SUBSEQUENT ANALYSIS OF COMPLEX CELL ARRANGEMENTS

(75) Inventors: Martin Stelzle, Reutlingen (DE); Brigitte Angres, Pfullingen (DE); Massimo Kubon, Muensingen (DE); Julia Schuette, Tuebingen (DE); Britta Hagmeyer, Tuebingen (DE); Felix Holzner, Langnau am Albis (CH)

(73) Assignee: NMI Naturwissenschaftliches und Medizinisches Institut an der Universitaet Tuebingen, Reutlingen (DE)

(*) Notice: Subject to any disclaimer, the term of this patent is extended or adjusted under 35 U.S.C. 154(b) by 0 days.

(21) Appl. No.: 12/896,714

(22) Filed: Oct. 1, 2010

(65) Prior Publication Data
US 2011/0079513 A1 Apr. 7, 2011

Related U.S. Application Data

(63) Continuation of application No. PCT/EP2009/002332, filed on Mar. 31, 2009.

(30) Foreign Application Priority Data
Apr. 3, 2008 (DE) .......... 10 2008 018 170

(51) Int. Cl.
*B01D 57/02* (2006.01)
(52) U.S. Cl. .............................. 204/547; 204/643
(58) Field of Classification Search .............. 204/547, 204/643
See application file for complete search history.

(56) References Cited

U.S. PATENT DOCUMENTS
5,470,739 A 11/1995 Akaike et al.
6,727,451 B1 4/2004 Fuhr et al.
(Continued)

FOREIGN PATENT DOCUMENTS
DE 198 15 882 10/1999
(Continued)

OTHER PUBLICATIONS
Ho et al., Lab Chip (2006) 6:724-734.
(Continued)

*Primary Examiner* — Kaj K Olsen
(74) *Attorney, Agent, or Firm* — Morrison & Foerster LLP

(57) ABSTRACT

A microfluidic system (12) for assembling and subsequently investigating complex cell arrangements has a three-dimensional microstructure (11) in which the cell culture is assembled, cultivated and investigated. At least two microchannel segments (16, 17) through which the microstructure (11) can be perfused from outside with a medium (21, 22) run in the microstructure (11), whereby the microchannel segments (16, 17) run at least in sections approximately parallel or equidistant to one another. The two microchannel segments (16, 17) are separated from one another by a wall structure (25) in which at least one aperture (26) connecting the two microchannel segments (16, 17) is provided. An electrode arrangement (27) is provided in or on the microstructure (11) in order to generate an inhomogeneous electric field (28) in the region of the at least one aperture (26). A cell arrangement is assembled in this microstructure (11) by supplying medium (21, 22) with cells (23, 24) for assembling the cell culture in the microstructure (11), with the inhomogeneous electric field (28) determined by the microstructure (11) bringing about the assembling of the cell arrangement from the supplied cells (23, 24).

10 Claims, 15 Drawing Sheets

U.S. PATENT DOCUMENTS

| | | | |
|---|---|---|---|
| 6,749,736 B1 * | 6/2004 | Fuhr et al. | 204/643 |
| 2001/0055882 A1 | 12/2001 | Ostuni et al. | |
| 2002/0164780 A1 | 11/2002 | Yao et al. | |
| 2004/0197931 A1 | 10/2004 | Indermuhle et al. | |
| 2004/0226819 A1 * | 11/2004 | Talary et al. | 204/451 |
| 2006/0196772 A1 * | 9/2006 | Kim et al. | 204/547 |
| 2007/0015137 A1 | 1/2007 | Zantl | |
| 2007/0015179 A1 | 1/2007 | Klapperich et al. | |
| 2007/0125941 A1 | 6/2007 | Lee et al. | |
| 2011/0079513 A1 | 4/2011 | Stelzle et al. | |

FOREIGN PATENT DOCUMENTS

| | | |
|---|---|---|
| DE | 198 53 658 | 5/2000 |
| DE | 199 52 322 | 5/2001 |
| DE | 10 2008 018 170 | 5/2010 |
| EP | 2 011 629 | 1/2009 |
| EP | 2 014 763 | 1/2009 |
| WO | WO-01/07583 | 2/2001 |
| WO | WO-2006/037033 | 4/2006 |
| WO | WO-2006/050617 | 5/2006 |
| WO | WO-2011/023655 | 3/2011 |

OTHER PUBLICATIONS

International Preliminary Report on Patentability for PCT/EP2009/002332, issued Oct. 5, 2010, 7 pages.

International Search Report for PCT/EP2009/002332, mailed on Jul. 28, 2010, 3 pages.

Nilsson, Human Cell (1992) 5:25-41.

Sebastian et al., J. Micromech. Microeng. (2006) 16:1769-1777.

Dewez et al., "Adhesion of mammalian cells to polymer surfaces: from physical chemistry of surfaces to selective adhesion on defined patterns," Biomaterials (1998) 19:1441-1445.

Goubko et al., "Patterning multiple cell types in co-cultures: a review," Materials Science and Engineering C (2009) 29:1855-1868.

Holländer et al., "Structured R2R Functionalisation of Polymer Film Surfaces by a Xenon Excimer Lamp," Plasma Process. Polym. (2007) 4:S1052-S1056.

Hook et al., "Patterned and switchable surfaces for biomolecular manipulation," Acta Biomaterialia (2009) 5:2350-2370.

International Search Report and Written Opinion for PCT/EP2010/062246, mailed Jan. 24, 2011.

Itoga et al., "Maskless liquid-crystal-display projection photolithography for improved design flexibility of cellular micropatterns," Biomaterials (2006) 27:3005-3009.

Patrito et al., "Spatially controlled cell adhesion via micropatterned surface modification of poly (dimethylsiloxane)," Langmuir (2007) 23(2):715-719 (abstract only).

Rabus et al., "A Bio-Fluidic-Photonic Platform Based on Deep UV Modification of Polymers," IEEE Journal of Selected Topics in Quantum Electronics (2007) 13(2):214-222.

Rhee et al., "Patterned cell culture inside microfluidic devices," Lab Chip (2005) 5:102-107.

U.S. Appl. No. 13/427,733, filed Mar. 22, 2012.

Wang et al., "Patterning bio-molecules for cell attachment at single cell levels in PDMS microfluidic chips," Microelectronics Engineering (2009) 86:1462-1464.

Welle et al., "Photo-chemically patterned polymer surfaces for controlled PC-12 adhesion and neurite guidance," Journal of Neuroscience Methods (2005) 142:243-250.

* cited by examiner

MICROFLUIDIC SYSTEM AND METHOD FOR ASSEMBLING AND FOR SUBSEQUENTLY CULTIVATING, AND SUBSEQUENT ANALYSIS OF COMPLEX CELL ARRANGEMENTS

This is a continuation application of copending international patent application PCT/EP2009/002332, filed Mar. 31, 2009, and designating the United States, which was published in English as WO 2009/121555 A2, and claims priority to German patent application DE 10 2008 018 170.6, filed Apr. 3, 2008. The contents of these prior applications are incorporated herein by this reference in their entireties.

BACKGROUND OF THE INVENTION

1. Field of the Invention

The present invention relates to a microfluidic system for assembling and for subsequently analysing complex cell arrangements, and to a corresponding method.

2. Related Prior Art

In many areas of scientific research and of diagnosis, whether in a research laboratory or in the daily work of a laboratory concerned with routine investigations, there is a need for complex cell arrangements which can be perfused under conditions which are as physiological as possible, meaning for example being present in the anatomically correct arrangement of the individual cell types relative to one another and/or physiologically functionally.

One example of the use of such complex cell arrangements is the determination of the toxicity and metabolism of medicaments in the pharmaceutical industry.

At present, the toxicity of medicaments is determined using 2 D cell cultures in vitro, but the predictive power thereof for the effect of the medicaments in vivo is only low. One reason for this is the fact that the currently available complex cell arrangements which can be used for corresponding investigations in vitro do not, owing to their structure and arrangement, exhibit the same properties as corresponding cell or tissue structures in vivo.

The result thereof is an only limited informative power of the experiments carried out with the known cell cultures in relation to behaviour (toxicity, metabolism, mechanisms of action) in vivo, so that for example side effects of medicaments are often discovered only in clinical studies when the product is administered to patients, and large expenditures have already been made for research and development.

Another approach to the determination of the toxicity of medicaments are animal experiments, but use thereof is declining, besides their informative power being only provisionally applicable to humans, also for ethical reasons.

A further approach consists of investigating the effect of medicaments on isolated cells, but the predictive power is also limited here, as with the abovementioned 2D cell cultures, since single cells or two-dimensional cell arrangements differ in essential with functions from those of the three-dimensional "natural" cell assemblage.

Hence there is a need for complex, organotypical cell culture systems consisting of "natural" cells which grow in environments which allow differentiation over an appropriately long period of time, and a function comparable to the in vivo situation.

Of particular interest in this connection is on the one hand an organotypical liver cell co-culture with which medicaments are to be tested for toxicity and metabolism. The liver serves inter alia for the degradation and excretion of metabolic products, medicaments and toxins which enter the liver via the circulatory system. These substances are metabolized by the hepatocytes and transported out with the bile fluid. The bile fluid produced by the liver enters the intestine via the biliary tract and is excreted in this way. It is important for an organotypical liver cell culture for medicament testing that the hepatocytes are, to the outside, invested by endothelial cells, and perfusion of the complex cell culture takes place from the side of the endothelial cells. The co-culture of hepatocytes with endothelial cells and, where appropriate, stellate cells ensures the tissue-typical differentiation of the hepatocytes and, associated therewith, expression of genes necessary for metabolizing the substances mentioned.

There is also a need for an organotypical tissue structure like that to be found for example in the intestine. In this case, too, it is necessary to distinguish between "inside" and "outside" for physiologically functional perfusion. Consumed substances are enzymatically cleaved in the intestine and transported into the blood stream via the intestinal epithelium. The intestinal epithelium consists of a monolayer epithelial layer facing the intestinal lumen, and an underlying layer of mesenchymal cells which maintains the differentiation and function of the epithelial cells. It would be possible to carry out investigations on the uptake of medicaments on oral administration in such a cell assemblage produced in vitro.

A further area of use is the so-called blood-brain barrier which controls the penetration of substances from the blood into the brain and ensures that the chemical composition of the intracellular fluids of the brain remains substantially constant, as is necessary for precise signal transmission between the nerve cells of the central nervous system. The blood-brain barrier is formed by endothelial cells and astrocytes around blood vessels. They ensure, via active transport systems, the transfer of nutrients and oxygen or metabolites. Knowledge about the permeability of the blood-brain barrier for active ingredients and thus their availability in areas of the nervous system is of particular interest in connection with the development of active ingredients.

The publication "Rapid Heterogenous Liver-Cell On-Chip Patterning via the Enhanced Field-induced Dielectrophoresis Trap" by Ho, et al., *Lab Chip,* 2006, 6, 724-734, discloses a microfluidic chip on which it is possible to establish a planar structure of liver cells, i.e., a 2D arrangement. An inhomogeneous electric field with defined gradients is generated through the geometric structure and arrangement of the electrodes and brings together cells of two cell types which are randomly present in a chamber to give a desired planar tissue pattern.

The authors mention that microfluidic patterning with microchannels and laminar flow cannot be applied to liver cells because this method is too coarsely structured in its effect. In addition, positive dielectrophoresis is described as a possible way of actively manipulating cells. However, the authors mention that this method has not yet been successfully employed to assemble complex cell arrangements.

With this background, the authors propose employing microfluidics together with a specially structured electric field in order to produce desired tissue patterns. For this purpose, the chip comprises a cell structuring chamber fed via microchannels continuously with cells which associate to give the complex structure via the electric field formed in the chamber. The electric field is then switched off, and pure medium is pumped through or into the chip.

The cell arrangement which can be generated with the known apparatus is, however, planar, so that the disadvantages described above arise for use in pharmacological research. It is not possible with the apparatus and the method of Ho, et al., to generate a complex cell arrangement which can be physiologically functionally perfused and can be employed as organotypical tissue for example for toxicity measurements.

SUMMARY OF THE INVENTION

In view of the above, it is an object of the present invention to provide an apparatus and a method of the type mentioned at the outset with which it is possible to assemble organotypical tissues which can then be perfused and investigated under preferably physiological conditions.

This object is achieved according to the invention by a microfluidic system for assembling and subsequently cultivating complex cell arrangements, comprising

- a three-dimensional microstructure in which the cell arrangement is assembled and cultivated,
- at least two microchannel segments running in the microstructure and defining a flow direction, through which microchannel segments the microstructure can be perfused from outside with a medium, whereby the microchannel segments run approximately parallel or equidistant to one another at least in sections,
- a wall structure which separates the at least two microchannel segments and in which at least one aperture connecting the at least two microchannel segments is provided, and
- an electrode arrangement provided in or on the microstructure in order to generate an inhomogeneous electric field in the region of the at least one aperture.

The object underlying the invention is further solved by a method for assembling and cultivating complex cell arrangements, in which method

- initially the complex cell arrangement is assembled in microfluidic system described above, by
- supplying medium with cells to the microstructure to assemble the cell arrangement, and
- generating in the microstructure an inhomogeneous electric field which is determined by a microstructure and which brings about the assembling of a cell arrangement from the supplied cells,
- and subsequently cultivating the cell arrangement in the three-dimensional microstructure by perfusing it with medium.

Finally, the present invention also relates to a method for investigating complex cell arrangements, in which method

- a cell arrangement is assembled and cultivated by the novel method in the novel microfluidic system, and
- the metabolism or directed transport of substances supplied to a cell arrangement established in this way is analyzed by means of discharged metabolic products and/or via markers which are supplied with the medium and which generate a measurable signal in cooperation with the cell arrangement.

The object underlying the invention is completely achieved in this way.

Namely, the inventors of the present invention have realized that with a respective design of the channel structure and application of the principles of dielectrophoresis it is possible to assemble complex organotypical cell arrangements.

The invention is based on the one hand on the positioning of cells with the aid of dielectrophoretic forces. Since these forces are directed in the direction of maximum field strength, the shape and position of the resulting microtissue can be predefined through a suitable inhomogeneous field.

In this connection, the inventors make use of a specific channel structure through which the position of maximum field strength is defined. For this purpose, at least two microchannel segments are provided in the microstructure and are separated from one another by a wall structure in which at least one aperture is provided. The microchannel segments run in the region of the wall structure in this case either straight and approximately parallel to one another, with bowed or curved microchannel segments also being possible as long as they run equidistant to one another at least in sections.

The inventors have been able to show in initial experiments that it is possible with the microstructure of the invention to assemble liver-like or membrane-like cell arrangements which can be cultivated and investigated under physiological conditions.

A further aspect of the invention consists of the inhomogeneity of the electric fields being predefined by the microstructure and influenced by the assembling cell arrangement itself. This is because accumulation of the cells at the position of highest field strength decreases the electrical impedance in this region, so that the field strength increases in the vicinity of this aggregate; there is thus a higher tendency for further accumulation of cells.

This increase in field strength can be measured and is an indication of the accumulation of the cells. This signal can, therefore, be used to control the amount of cells that aggregate in the aperture. If the desired amount of cells has been reached, the supply of these cells will be terminated and/or the electric field is switched of or to another frequency/voltage combination for accumulation of cells of a different type.

The invention is further based on the realization that it is possible by two microchannel segments which in sections run approximately parallel or equidistant, and which are separated from one another by a wall structure with at least one aperture, to set up an electric field with a defined inhomogeneity and of which the highest field strength is located in the region of the aperture in the wall structure, and which is suitable for assembling complex cell arrangements.

Because the electric field has its highest field strength in the region of the apertures, the cells supplied through the two microchannels are concentrated in the region of these apertures and assembled there. Owing to this field structure, the cells can moreover not pass from one microchannel into the other.

Finally, the novel microfluidic system makes it possible to analyse optically and/or biochemically the established complex cell arrangement.

After the complex cell arrangement has been assembled in the microstructure, the inhomogeneous electric field can be switched off, but it can also continue to be applied unchanged or with changed field strengths and/or frequencies.

The prior art discloses microfluidic systems having microchannel segments separated by wall structures and connected with each other via openings in said wall structures, wherein electrodes are arranged. However, none of the prior art documents discloses or teaches to establish an inhomogeneous electric field in the region of the openings such that cells supplied via the microchannel segments can aggregate within the opening and form complex cell arrangements.

DE 198 15 882 A1 discloses a microfluidic systems wherein electrodes are located on top and bottom plates, forming a dielectrophoretic deflector unit intended to move particles from on channel to another by negative dielectrophoresis. The electric field extends vertically, having maxima at the electrode edges and minima in the middle of the channel. The known electrode arrangement cannot create a lateral field non-homogeneity and, therefore, cannot trap particles.

The opening in the wall does not comprise a variation of cross-section as would be necessary to create a lateral field non-homogeneity. The known system is neither intended nor can it be used to trap particles in the opening.

DE 198 53 658 A1 discloses a comparable system with an arrangement of electrodes to form deflector units operating by making use of negative dielectrophoresis. Particles are separated laterally and sedimented at the bottom end of the system by centrifugal forces. There is no opening with an electric field non-homogeneity created in it that could be used to trap particles by positive dielectrophoresis.

According to DE 199 52 322 C2 several channels communicate through an opening in a wall. However, as in the prior art discussed above, there is no lateral variation of cross-section in the wall opening, i.e., no lateral field non-homogeneity useful for trapping by positive dielectrophoresis is possible. Further, electrodes are located on top and bottom walls and are operated in negative dielectrophoresis mode. Trapping of individual particles is performed by means of optical tweezer technology or dielectrophoretic field cages using negative dielectrophoresis rather than utilizing 3D-micropatterned insulator structures.

According to US 2002/0164780 A1 cells are cultivated in a channel of constant cross-section. Cells are kept in place by means of mechanical trapping prepared by electroplating of gold rather than by electrical forces of any kind. Even though there are various electrodes deposited within the channel, due to the homogeneous cross-section of the channel, these electrodes cannot be used and are not intended to trap cells in the cultivation module because they cannot create an inhomogeneous electric field at the location of the cultivation module. Rather, the electrodes are used as electrohydrodynamic and electroosmotic pumps.

US 2004/0197931 A1 describes an arrangement of a number of parallel microchannels with openings intended to move a sensor from one channel to another to quickly measure characteristics of different media flowing through the channel. There is no mentioning of an electrode being placed on lateral walls in order to measure or create an electric field. This document shows a microprobe reaching into the slot formed by the many wall openings, which can be moved to establish contact to the media flowing in the channels.

To the contrary, and as already mentioned above, the system of the present invention uses positive dielectrophoresis to trap cells in an opening or aperture.

According to the invention, it is preferred that the microchannel segments are either each part of a separate microchannel which runs through the microstructure, or combine into a common microchannel in front of and behind the wall structure.

If a common microchannel is provided, the same medium flows through both microchannel segments. The advantage here is that, for example, to assemble a liver structure, cells of the same cell type migrate out of both microchannel segments into the region of the aperture(s) and are assembled there. After an inner cell arrangement composed of cells of a first cell type has been assembled in this way, cells of a second cell type can be supplied with the medium and accumulate from both microchannel segments on the inner cell arrangement and form an outer cell arrangement. It is subsequently possible to supply cells of a third cell type forming a second outer cell arrangement, and so on.

It will be appreciated that mixtures of different cell types can also be supplied in each case to assemble the inner and each outwardly following outer cell arrangement.

If separate microchannels are provided, different medium can be supplied on both sides of the wall structure. The advantage here is that, for example, to assemble a layered cell arrangement, it is possible to supply and accumulate simultaneously cells of different cell types on the sides remote from one another of the aperture(s), which then assemble on their respective side their own cell arrangements which may in each case consist of cells of one or more cell types.

A further advantage is that it is possible to supply through one of the separate microchannels for example medium with nutrients and, where appropriate, test substances, whereby metabolic products can be removed through the other microchannel and subjected to analysis.

With the novel microfluidic system it is moreover preferred on the one hand for the at least one aperture to have a slot extending in the direction of flow of the two microchannel segments, with preferably a plurality of slots being arranged in succession in the direction of flow.

It is preferred on the other hand for a plurality of apertures to be provided and be arranged distributed in the wall structure in the direction of flow of the two microchannel segments and perpendicular to the direction of flow.

If the aperture is designed in the form of one or more slots extending in the direction of flow of the microchannels or microchannel segments, it is possible, for example, to assemble a three-dimensional liver structure. If, however, many pore-like apertures are arranged distributed uniformly or non-uniformly over the wall structure, a layered cell arrangement can be formed.

It is further preferred for the electrode arrangement to have at least one channel electrode provided in the first microchannel segment and at least one further channel electrode provided in the second microchannel segment, with channel electrodes being provided in the vicinity of the at least one aperture or further apertures, with preferably at least one channel electrode in each microchannel segment being arranged on a wall opposite the wall structure, it being even further preferred for at least one channel electrode in each microchannel segment to be arranged on a wall adjoining the wall structure.

Depending on the cell arrangement to be established, and appropriate for the shaping of the aperture(s), it is thus possible to generate the inhomogeneous field which is optimal for the respective application and through which the cells are transported out of the microchannel segments into the aperture(s) and assembled there. It is thereby possible to arrange the channel electrodes in interdigitated fashion, so that as compared with one pair of channel electrodes each channel electrode pair can be supplied with respectively lower voltages since many apertures are connected in series.

Finally, it is preferred for the wall structure to have two webs which face one another with their front surface and, between them, define at least one slot, where preferably at least one of the two webs is designed to have a rectangular, trapezoidal, triangular or crowned cross section and/or at least one of the two webs has on its front surface a ridge running in the direction of flow.

The advantage here is that the shape of the inhomogeneous electric field is partly determined by the shape of the slot resulting from the shape of the web. The region of maximum field strength can thus be optimally adjusted for the respective application.

It is further preferred for the electrode arrangement to have at least two web electrodes which are provided on the webs and which are preferably arranged oppositely in the direction of flow and/or are arranged at least on the front surface of one of the two webs.

The advantage here is that cells are concentrated on or at the webs and are lined up between the web electrodes for example like a pearl chain.

It is then preferred for at least one further microchannel to run between the at least two microchannel segments and to be in fluidic connection with the at least one aperture.

The advantage here is that metabolic products can be transported away from the aperture. With a liver structure, the further microchannel is in this case connected only to the hepatocytes. This is because in a tissue structure similar to the liver sinusoid, the small bile ducts of the individual hepatocytes connect together to form a common bile duct with an axis parallel to the (external) direction of perfusion along the endothelial cells.

The further microchannel can in this case either run "through the aperture" or be connected to the aperture on only one side. In the case of a tissue structure similar to the liver sinusoid, it is preferred for the further microchannel to be connected only on one side to the aperture as a bile duct in order to remove the bile "physiologically", meaning contrary to the direction of flow of the medium in the two microchannel segments.

The novel microfluidic system is preferably provided with connectors for fluidic control.

The advantage here is that the flow through the two microchannel segments can be controlled in such a way that no cross flow through the aperture(s) is forced. This can take place, for example, by controlling the inflow rates for both microchannel segments and the outflow rate for one of the two microchannel segments, whereby the outflow rate in the other microchannel segment inevitably results. With an appropriate setting of the flow rates, crossflow through the aperture(s) in the wall structure is precluded.

It is further preferred for the microstructure to be provided in different regions with different selective coatings.

The advantage here is that the colonization of particular regions of the microstructure can be assisted by an adhesive coating or prevented by a non-adhesive coating—e.g., in the channel segments. A further possibility is to provide a coating with extracellular matrix in order to assist cell growth and differentiation. It is furthermore possible after assembling a first type of cells to flush with a medium with (extracellular matrix) molecules which mediate cell-cell interaction in order to produce a functional contact with cells of a further cell type which are introduced in to the microsystem in a further, following step.

It is also preferred in general for at least one dielectric structure to be provided in the region of the at least one aperture for influencing the electric field.

The advantage of this measure is that the field strength in the region of the aperture(s) can be modulated specifically in order to achieve a particular arrangement of the cells.

It is preferred in the novel method for initially first cells to be supplied to the microstructure through the two microchannel segments to assemble a cell arrangement, and thereafter to supply second cells different from the first cells in order to assemble on the cell arrangement composed of the first cells a cell arrangement composed of the second cells, it being possible for the first cells to be hepatocytes and for the second cells to be endothelial cells.

After for example a first cell type has been assembled in a slot or in apertures in this way, a second cell type can be passed through the microchannel segments and then collects on the outside of the aggregate of the first cells, so that the first cells are completely shielded by the second cells in relation to the first and the second microchannel.

It is possible in this way, for example, to generate an organotypical liver tissue in which the first cells are hepatocytes and the second cells are endothelial cells. After this complex structure has been assembled, it is then perfused with nutrient fluid through both microchannels and thus cultivated over prolonged periods of time. If medicaments are now added to the medium, they can be tested for toxicity and metabolism. It is advantageous in this connection that the hepatocytes are completely invested by endothelial cells, so that the perfusion of the complex cell culture takes place from the side of the endothelial cells, as is the case in intact liver tissue.

On the other hand, it is preferred for the microstructure to be supplied through the first microchannel segment with first cells and through the second microchannel segment with second cells different from the first cells, it being possible for the first cells to be astrocytes or intestine-typical mesenchymal cells and for the second cells to be epithelial cells.

In this case, cell types different from one another are supplied simultaneously or successively in the two microchannel segments, so that first cells from the first microchannel segment, and second cells from the second microchannel segment, assemble in and on the aperture, and a bilayer tissue structure of two different cell types results. After this complex cell arrangement has been assembled, the first cells come into contact only with the medium in the first microchannel segment, and the second cells come into contact only with medium in the second microchannel segment.

It is possible in this way to establish the blood-brain barrier through endothelial cells and astrocytes. In connection with the development of active ingredients it is now possible to determine the permeability of the blood-brain barrier for these active ingredients and thus their availability in regions of the nervous system.

A further possibility is to establish the structure of the intestinal epithelium by mesenchymal cells and epithelial cells and to measure the transport of active ingredients through the intestinal epithelium and thus their availability for entry into the vascular system.

"First cells" and "second cells" mean in the context of the present invention not only cells of a single cell type but also mixtures of cells of different cell types. Thus, for example, stellate cells can be admixed with the endothelial cells in the assembling of a liver structure.

It is generally preferred for the cell arrangement to be supplied with nutrients and/or test substances together with the medium and/or for metabolic products to be removed from the cell arrangement through one of the two microchannels or a further microchannel.

It is thus possible to add markers to the nutrient fluid in order to investigate the response of the organotypical cell tissue to these substances. These may be fluorescent markers such as, for example, antibodies which bind cell-specifically and thus make it possible to investigate the actual cell arrangement.

A further possibility is to perfuse the cell arrangements with test substances and/or medicaments whose effect, transport or metabolism are to be investigated in the established cell arrangement.

It will be appreciated that the features mentioned above and to be explained hereinafter can be used not only in the combination indicated in each case, but also in other combinations or alone, without departing from the scope of the present invention.

BRIEF DESCRIPTION OF THE DRAWINGS

Further advantages are evident from the following embodiments and in connection with the drawings, in which.

DESCRIPTION OF PREFERRED EMBODIMENTS

Figure 1:
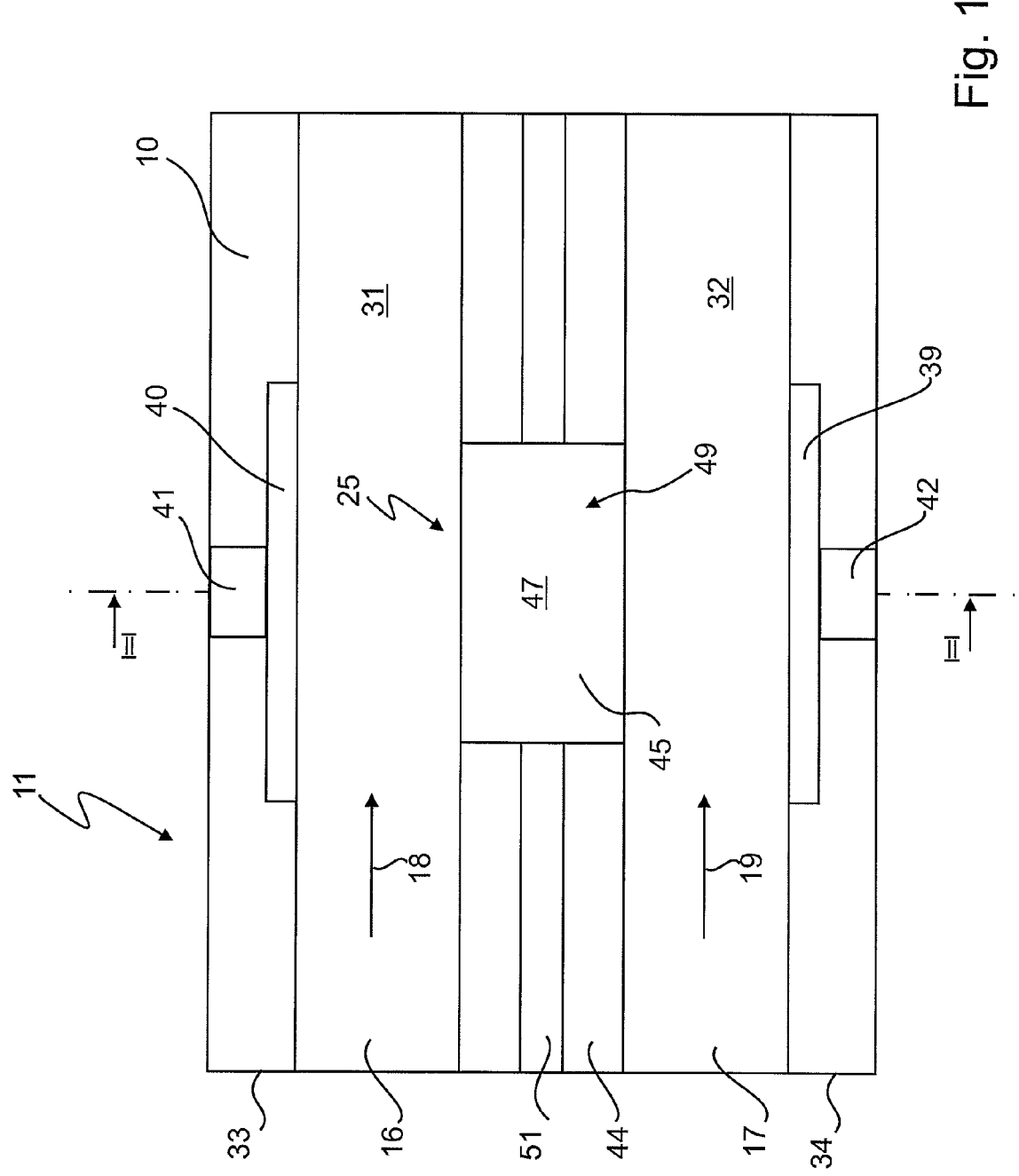
FIG. 1 shows a diagrammatic plan view, in the form of a detail not true to scale, of a lower part of a first embodiment of a microstructure of the novel microfluidic system along line I-I from FIG. 2.

FIG. 1 depicts a diagrammatic plan view, in the form of a detail not true to scale, of a lower part 10 of a first embodiment of a microstructure 11 of a microfluidic system.

Figure 2:
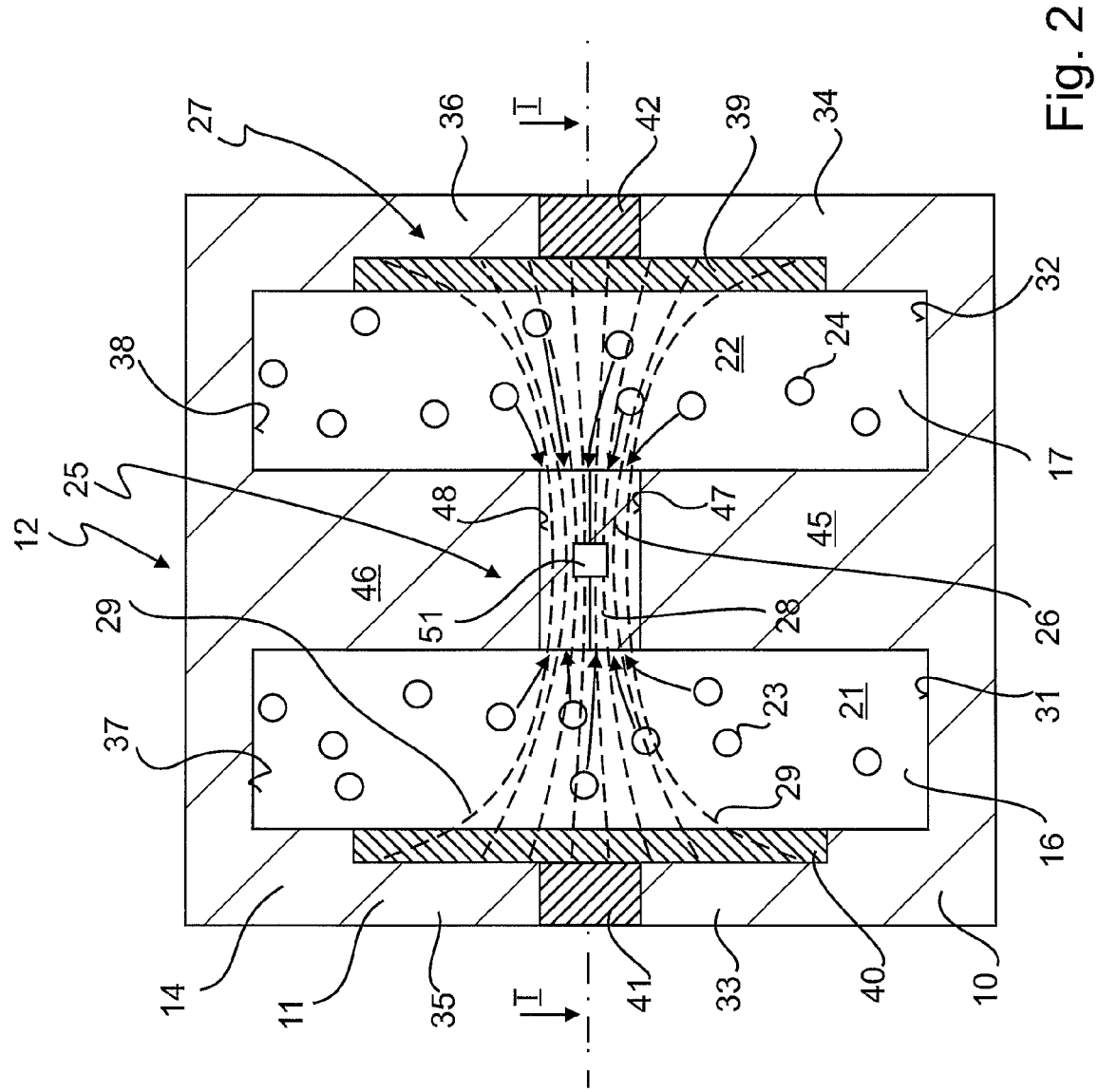
FIG. 2 shows a diagrammatic depiction not true to scale of a section through the microstructure of FIG. 1 along line II-II therein.

FIG. 2 shows a section transversely through the microfluidic system 12 along the line II-II in FIG. 1, while the plan view in FIG. 1 is viewed along the line I-I in FIG. 2.

The microstructure 11 has an upper part 14 which corresponds in geometric structure to the lower part 10 and which closes the lower part 10.

Two microchannel segments 16, 17 run through the microstructure 11 in parallel with and at a distance from one another, which are formed, in the example shown, partly in the lower part 10 and partly in the upper part 14. It is, of course, possible also for the microchannel segments 16 and 17 to be formed entirely in the lower part 10 or in the upper part 14, and then the upper 14 and the lower part 10 forming merely a channel cover and channel base, respectively.

The microstructure 11 is perfused from outside through the microchannel segments 16, 17, in the directions of flow 18 and 19 defined by the microchannel segments 16, 17, with medium which is indicated at 21 and 22 in FIG. 2. Nutrients and test substances can be supplied, and metabolic products removed, with the medium 21, 22. It is furthermore possible for cells 23, 24 to be transported in the medium 21, 22, and to assemble to a complex cell arrangement in a manner yet to be described.

The microchannel segments 16, 17 are separated from one another by a wall structure 25 in which an aperture 26 is provided that connects the two microchannel segments 16, 17 with each other.

Also provided in the microstructure 11 is an electrode arrangement 27 by which an inhomogeneous electric field 28 is generated in the region of the aperture 26, some field lines 29 of which are depicted as broken lines by way of example in FIG. 2.

This field 28 moves the cells 23, 24 towards the aperture 26, where they assemble and form a complex cell arrangement not shown in FIG. 2. In this case, use is made of the effect of field-induced dielectrophoresis described for example in the publication by Ho, et al., mentioned at the outset.

It is evident in FIGS. 1 and 2 that the lower part 10 has outer walls 33, 34 which extend from the respective channel base 31, 32 upwards and correspond to outer walls 35, 36 on the upper part 14 which extend from the respective channel cover 37 or 38. The outer walls 33, 34, 35, 36 are in contact with one another via their front surfaces which are to face one another.

Figure 3:
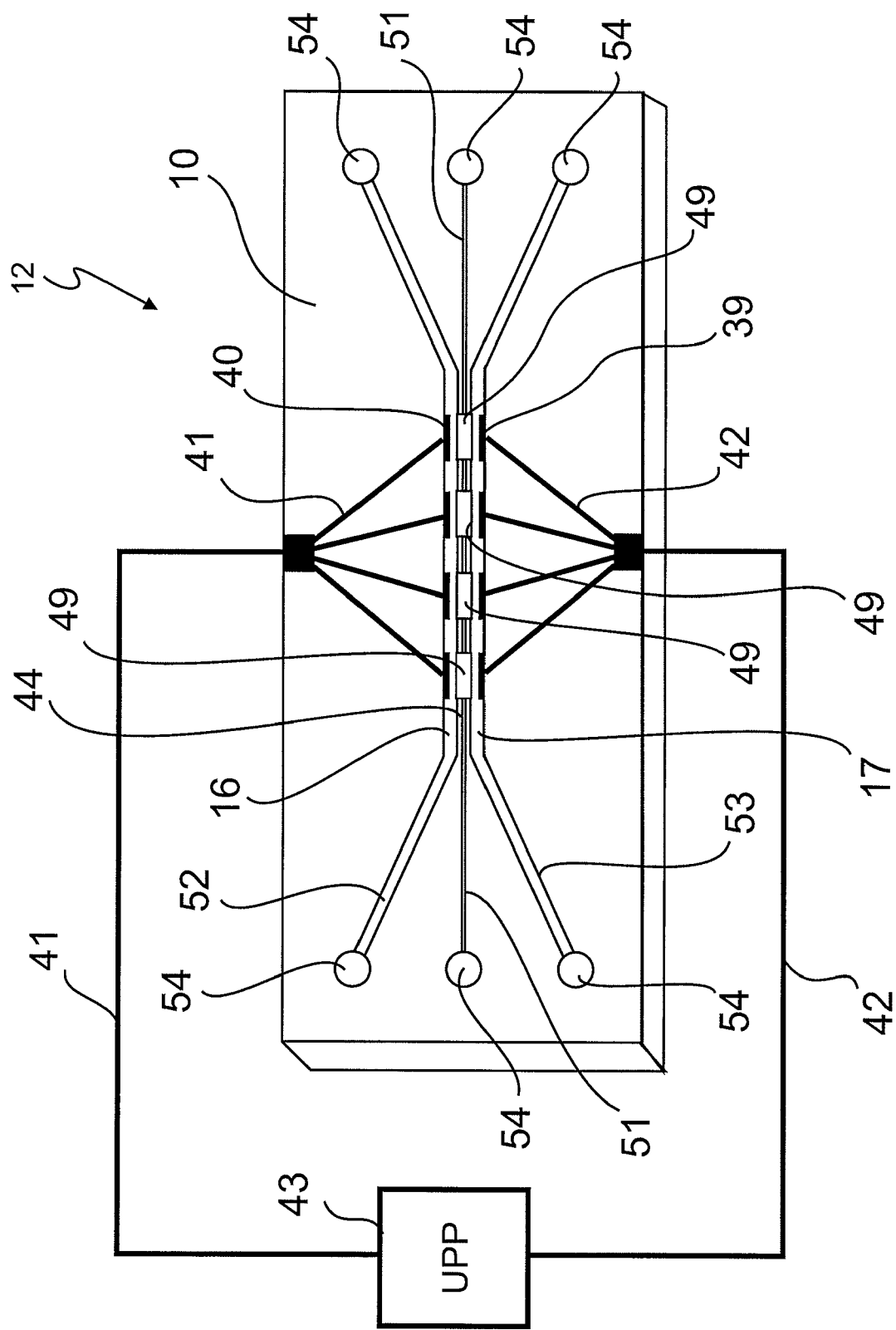
FIG. 3 shows in a depiction as in FIG. 1 an overall plan view of the novel microfluidic system of FIGS. 1 and 2, with the upper part removed, in which a plurality of slots are arranged serially one after the other.

Channel electrodes 39 and 40 of the electrode arrangement 27 are arranged in or on the outer walls 33, 34, 35, 36 opposite the aperture 26 and can be connected via leads 41 and 42, respectively, to an electrical AC voltage generator 43 which is to be seen in FIG. 3 and has a variable frequency f and variable voltage swing Upp.

The wall structure 25 includes a partition 44 which is formed by appropriate regions of upper part 14 and lower part 10 which, like the outer walls 33, 34, 35, 36, are in contact with one another. In the region of the aperture 26, the partition 44 is formed with webs 45, 46 which are set back from the contact area and whose front surfaces 47 and 48 face one another and limit the aperture 26 between them.

The webs 45, 46 run in the direction of flow 18, 19, so that the aperture 25 has the shape of an elongate slot 49.

A further microchannel 51 runs in the partition 44 parallel to and between the microchannel segments 16, 17 and is in fluidic connection to the slot 49, so that material can be removed from the region of the slot 49.

The further microchannel 51 can moreover pass through the slot 49—as shown in FIG. 1—that is to say be connected on both sides to the slot 49 and the aperture 26, respectively, but it may also be provided only on one side of the slot 49, which is advantageous in particular for investigating organotypical liver structures when the further microchannel 51 serves as bile duct.

The microstructure 11 is fabricated from a dielectric material, so that the field structure is also determined by the geometry described insofar. The field 28 has its highest field density in the region of the slot 49, the shape of the field being essentially determined by this geometry, and the field strength by the voltage swing Upp.

The material which has proved suitable for the microstructure 11 is glass, silicon, where appropriate with an insulating layer, e.g., of silicon oxide or silicon nitride, and polymers such as, for example, PMMA, polystyrene, PEEK, COC (cyclic olefin copolymer). Transparent, nonconductive materials are preferably employed, and the above list should be understood as only by way of example.

The microstructure 11 can be produced by suitable methods known per se for microstructuring, such as, for example, photolithography in combination with plasma etching methods or wet-chemical etching methods, and in the case of polymer materials by microinjection moulding or hot embossing.

The length of the slot 49 in the direction of flow 18, 19 is for example 20 to 2000 μm, preferably about 1500 μm. The height of the slot 49 between the front surfaces 47, 48 is for example 10 to 100 μm, preferably about 50 μm. The width of the slot 49 on the front surface 47, 48 perpendicular to the direction of flow 18, 19 is for example 10 to 200 μm, preferably about 100 μm.

The height of the microchannel segments 16, 17 between channel base 31, 32 and channel cover 37, 38 is for example 50 to 2000 μm, preferably about 500 μm. The width of the microchannel segments 16, 17 between outer wall 33, 34, 35, 36 and partition 44 is for example 20 to 2000 μm, preferably about 200 μm.

The width of the further microchannel 51 perpendicular to the direction of flow is about 5 to 10 μm. The length of the channel electrodes 39, 40 in the direction of flow 18, 19 is greater than the length of the slot 49, and the height of the channel electrodes 39, 40 perpendicular to the direction of flow is greater than the height of the slot 49 between the front surfaces 47, 48.

These dimensional statements and size relationships are to be understood as merely by way of example, and they may vary depending on the cells 23, 24 to be assembled.

It is important in this connection that by means of the geometry of the microstructure 11 an inhomogeneous field is set up, for which purpose it is not absolutely necessary for the dimensions of the channel electrodes 39, 40 to be greater than those of the slot 49. When the microstructure 11 is filled with medium, the electrical resistance between the channel electrodes 39, 40 varies over the distance between the channel electrodes 39, 40, leading to the setting up of an inhomogeneous field 28.

As already mentioned, the microstructure 11 is suitable for example for establishing an organotypical liver structure. Hepatocytes have a diameter of about 50 μm, with two rows each of about 20 to 30 hepatocytes being arranged in succession in a liver sinusoid. The optimal dimensions for the slot 49 resulting therefrom are a width of 100 μm, a height of 50 μm, and a length of from 1000 to 1500 μm.

An embodiment revealed in FIG. 3 is one in which the microchannel segments 16, 17 have a total of four slots 49 in succession in the direction of flow, to each of which dedicated leads 41 and 42 for channel electrodes 39, 40 lead.

The microchannel segments 16, 17 are in this case each part of a separate microchannel 52 or 53, between which the further microchannel 51 runs that connects all four slots 49 together.

All three microchannels 51, 52, 53 have at their ends connectors 54 for fluidic control in order to be able to adjust the flow rate of the medium individually in microchannels 51, 52, 53.

The flow of the mediums through the two microchannels 52, 53 can moreover be controlled in such a way that no cross flow is forced through the slot 49.

The microstructure 11 is in this connection provided in different regions with different selective coatings. In this case, colonization in the region of the slot 49 can be assisted by an adhesive coating, and prevented in the microchannels 52, 53 by a non-adhesive coating. It is furthermore possible to provide a coating with extracellular matrix in order to assist cell growth and differentiation.

It is now possible with the microfluidic system 12 described insofar to assemble an organotypical, complex cell arrangement. If, for example, a liver structure is to be established, initially hepatocytes are added to the medium 21 and 22 in the two microchannels 52 and 53, respectively, and are deposited in the slots 49 owing to the structure of the inhomogeneous field 28. As already mentioned at the outset, the dielectrophoretic forces lead to the cells being moved in the direction of the greatest field density.

After hepatocytes have assembled in the slots 49 in this way, a second cell type, in the present case therefore endothelial cells, is now added to the medium 21 or 22, which are deposited on the outside of the hepatocyte structure and finally isolate the latter completely in relation to the media 21, 22.

It is now possible to supply through microchannels 52 and 53 nutrients and test substances, while the metabolic products can be removed from the slots 49 which are serially connected together through the microchannel 51 and in which the cell arrangements have assembled.

The assembling of an organotypical liver structure is, of course, only one example of the application of the novel microfluidic system.

Figures 4, 5:
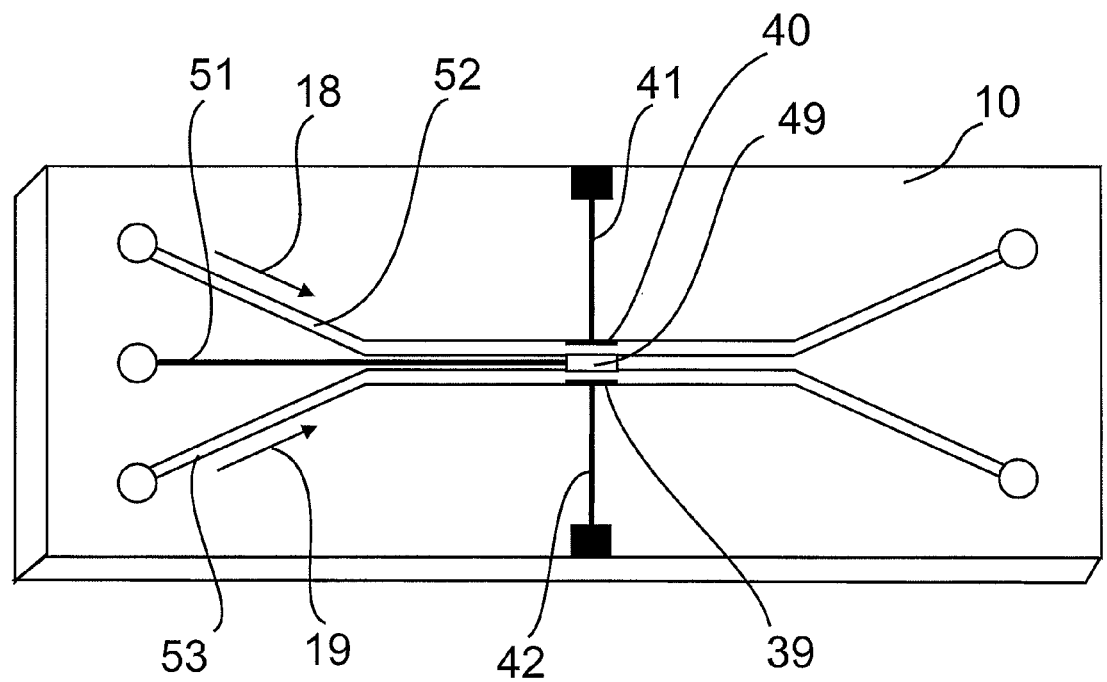
FIG. 4 shows in a depiction as in FIG. 3 a microfluidic system in which the further microchannel is connected on only one side to the slot.
FIG. 5 shows in a depiction, in the form of a detail, as in FIG. 3 or 4 a microfluidic system in which a plurality of slots are arranged parallel to one another.

In FIG. 3, four slots 49 which are connected in series and are connected together by a common microchannel 51 are provided. However, it is also possible—as already mentioned above—to provide only one slot 49 which is connected on only one side to the microchannel 51, as shown in FIG. 4. The microchannel 51 then runs against the direction of flow 18, 19.

It is also possible, on the other hand, to provide the slots 49 parallel to one another, by arranging a plurality of wall structures or partitions 44 beside one another perpendicular to the direction of flow 18, 19, as shown in the form of a detail in FIG. 5 for three slots 49. Each slot 49 is then connected via its own microchannel 51' to the common microchannel 51.

In FIG. 5, the leads to the channel electrodes 39, 40 and the microchannels 52, 53 are not shown for reasons of clarity. The microchannel segments 16, 17 and the microchannels 51, 51', and the leads to the electrodes which are not shown, must where appropriate be arranged in different planes—parallel to the plane of the drawing—in order to avoid problems at possible crossing points.

Figure 6:
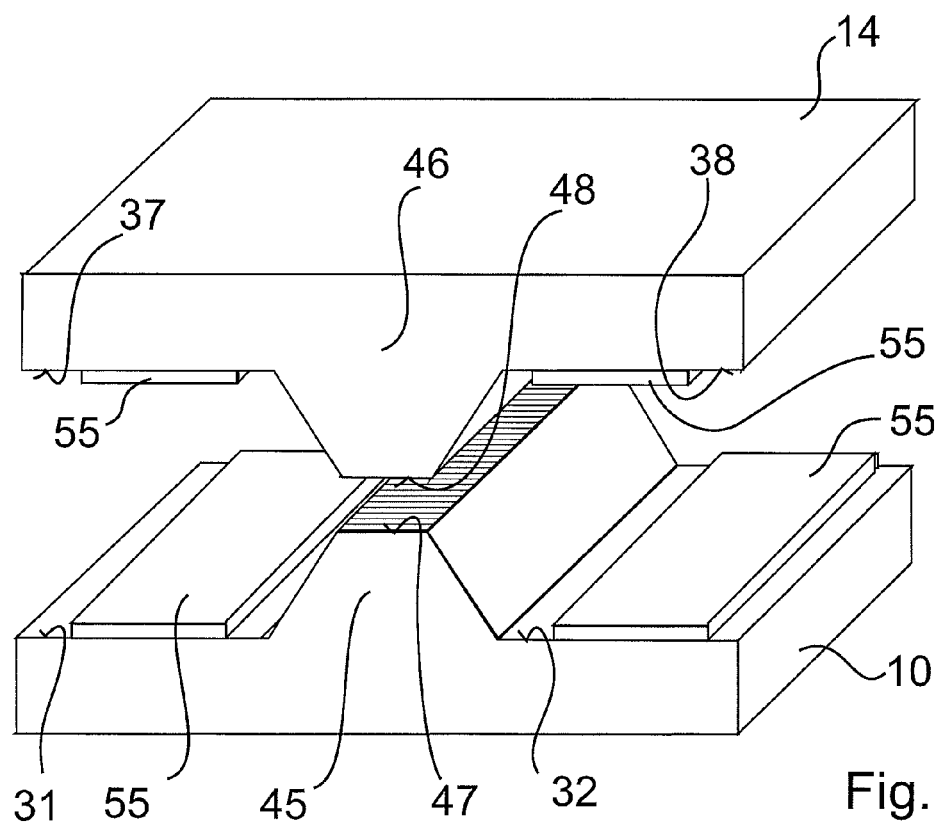
FIG. 6 shows in a depiction as in FIG. 2 a perspective view of a further embodiment of the novel microfluidic system in the region of the wall structure, with channel electrodes being provided on the channel base and cover.
Figure 7:
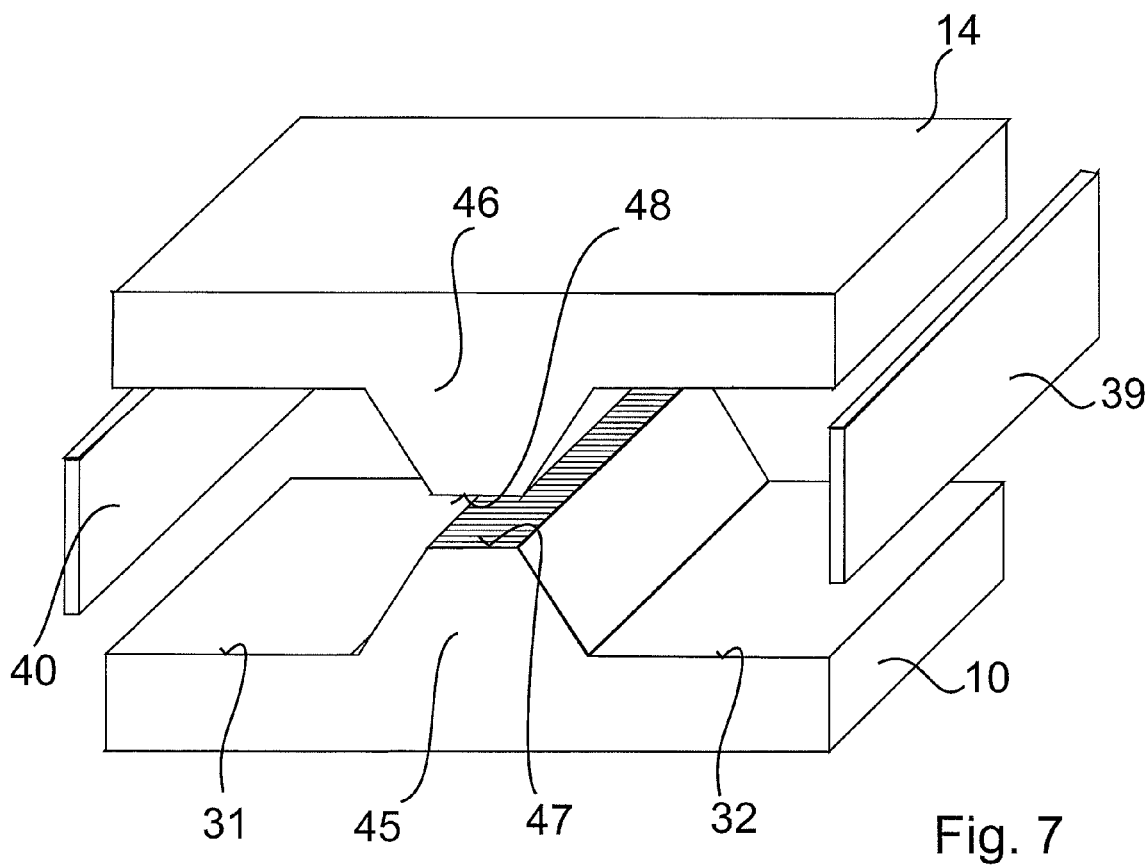
FIG. 7 shows in a depiction as in FIG. 6 a further embodiment of the novel microfluidic system in the region of the wall structure, with channel electrodes being provided on the side walls.

Whereas the webs 45 and 46 in the embodiment of FIGS. 1 to 5 have a rectangular cross section, the webs may also be designed to be trapezoidal as shown in FIGS. 6 and 7. It is possible, through the trapezoidal web structure, to influence the inhomogeneous electric field further, so that a field structure which is particularly suitable for assembling cells results.

Whereas in FIG. 7 the channel electrodes 39, 40 are arranged as in FIGS. 1 and 2 on the outer walls which are not shown in FIG. 7, in the embodiment shown in FIG. 6 channel electrodes 55 are arranged on the channel base 31, 32 and on the channel cover 35, 38. In a further embodiment, several pairs of channel electrodes may be provided between the walls.

It is, of course, also possible to provide channel electrodes both on the outer walls and on the channel base and channel cover.

The inhomogeneous field which is forming can be influenced further by the chosen arrangement of the channel electrodes 39, 40, 55.

Figure 8:
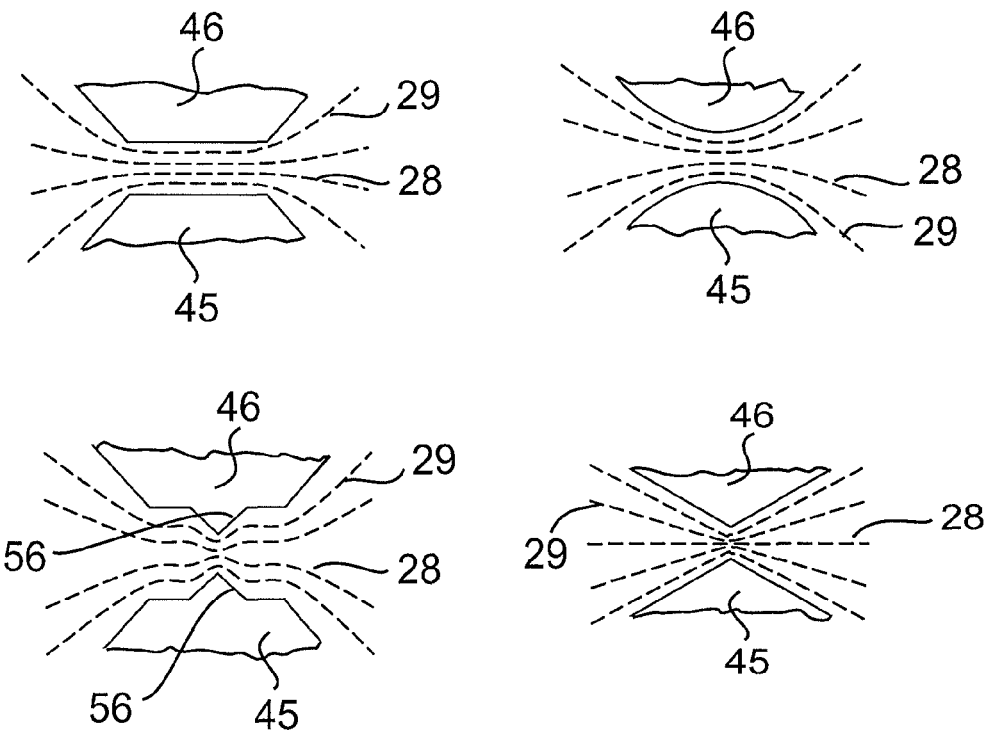
FIG. 8 shows four diagrammatic sectional depictions, not true to scale, of different web shapes in the embodiment of FIG. 6 or 7.
Figure 9:
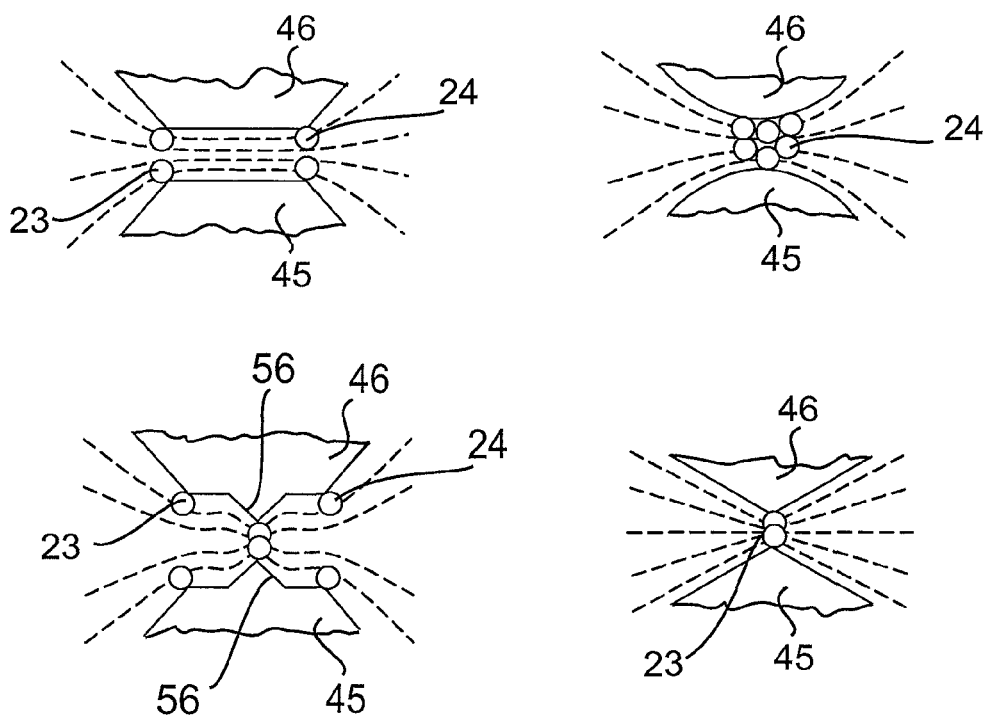
FIG. 9 shows in a depiction as in FIG. 8, by way of example, the assembling of cells on the webs of the wall structure.

FIGS. 8 and 9 show in each case four web shapes in cross section; the cross section of the web 46, 47 is in each case trapezoidal top left, circular top right, triangular bottom right and trapezoidal with ridges 56 following in the direction of flow bottom left.

FIGS. 8 and 9 show again as broken lines field lines 29 of the inhomogeneous electric field 28 which is forming, it further being evident from FIG. 9 how cells 23, 24 are arranged in the respective slot 49. The principle common to all the structures is that one or more field maxima form in the constriction(s) and define the position of the cells 23, 24.

Figure 10:
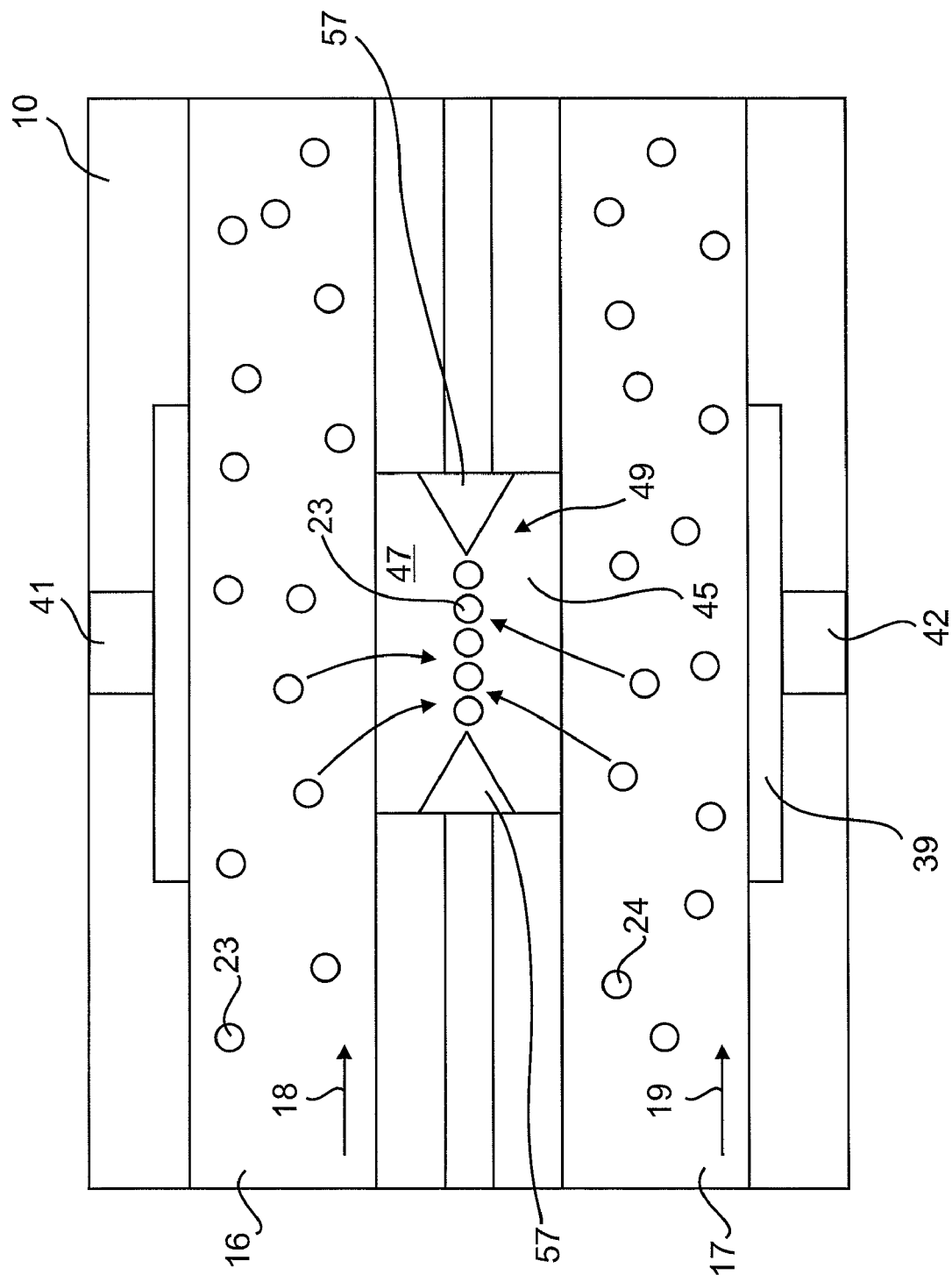
FIG. 10 shows in a depiction as in FIG. 1 a further embodiment of the novel microfluidic system in which web electrodes are arranged on the web.

FIG. 10 shows in a depiction as in FIG. 1 a lower part 10 of a microstructure, where web electrodes 57 which are facing one another are provided on the front surface 47 of the web 45 in the direction of flow 18, 19, between which cells 23 form a pearl-chain arrangement. It is thus possible to influence through the additional web electrodes 57 the structure of the organotypical tissue forming in the slot 49.

Figure 11:
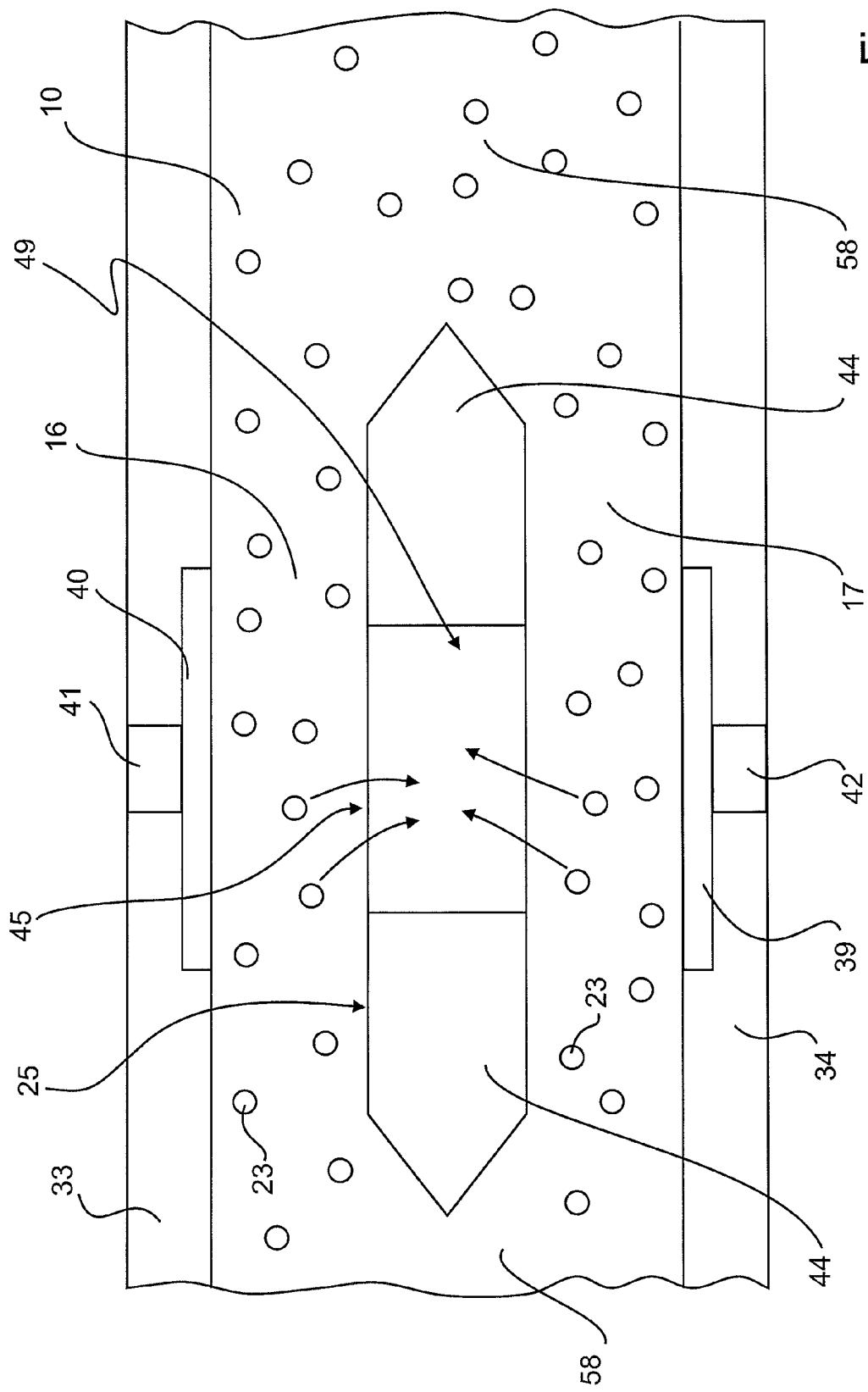
FIG. 11 shows in a depiction as in FIG. 1 a further embodiment of the microstructure of the novel microfluidic system in which the two microchannels unite to one microchannel in front of and behind the wall structure.

FIG. 11 shows in a depiction as in FIGS. 1 and 10 a further embodiment of the novel microstructure 11 in which the microchannel segments 16 and 17 unite to a common microchannel 58 in front of and behind the wall structure or partition 44.

Whereas it is possible with the microstructures in FIGS. 1 and 10 to supply cells of different cell types simultaneously through the microchannel segments 16 and 17, so that first cells from microchannel segment 16 and, simultaneously, second cells 24 from microchannel segment 17 assemble in the slot 49, in the microchannel structure 11 in FIG. 11 only cells 23 of one cell type are supplied simultaneously, as can take place when assembling an organotypical liver structure.

Figure 12:
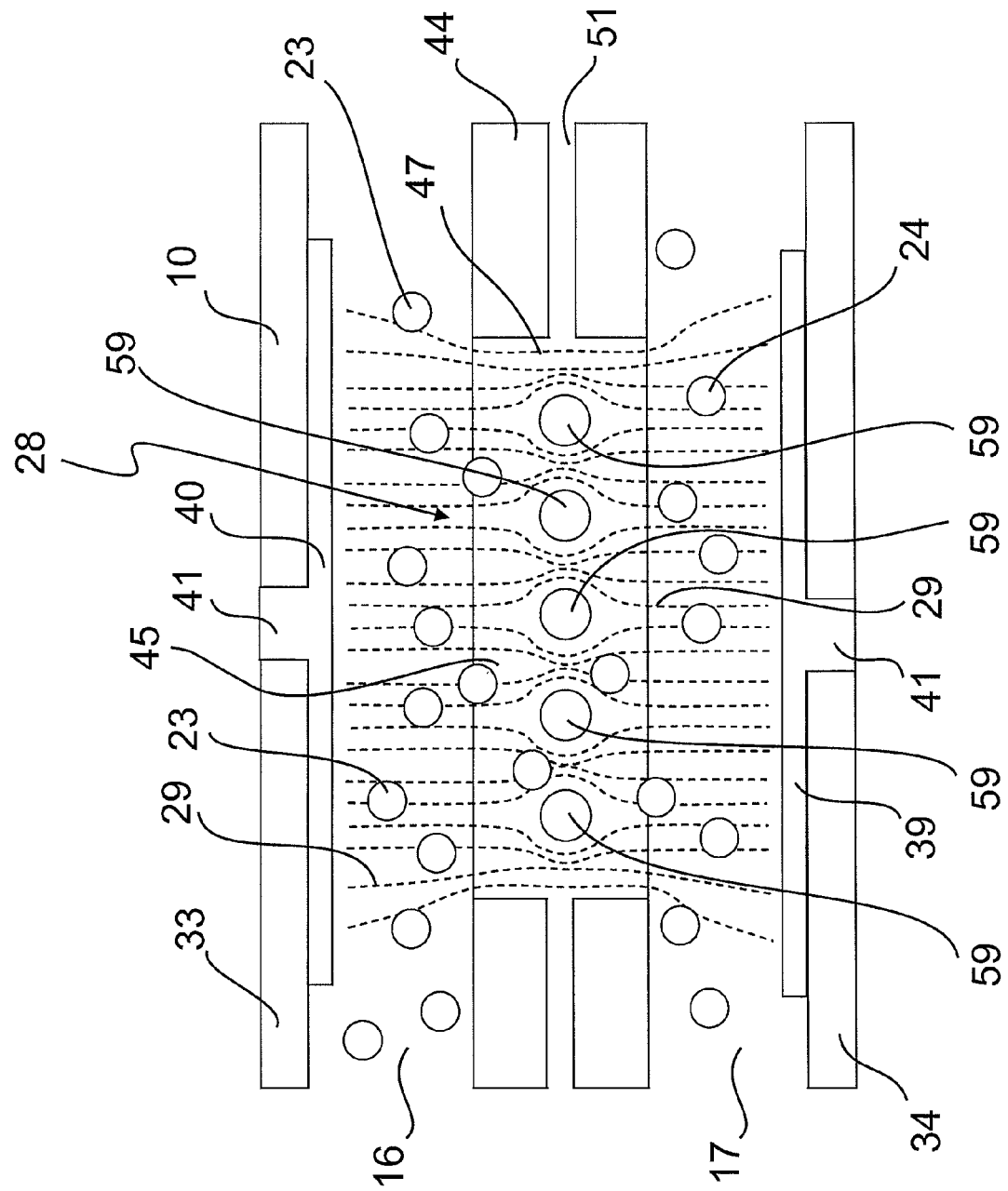
FIG. 12 shows in a depiction as in FIG. 1 a further embodiment of the novel microfluidic system in which dielectric structures for modulating the field strength are provided on the web.

FIG. 12 shows in a depiction as in FIG. 1 a microchannel structure in which a total of five further dielectric structures 59 are provided on the front surface 47 of the web 45, which structures are here formed as round posts and further influence the inhomogeneous electric field 28, as is evident from the course of the field lines 29, and bring about an appropriate arrangement of the cells 23, 24.

Figure 13:
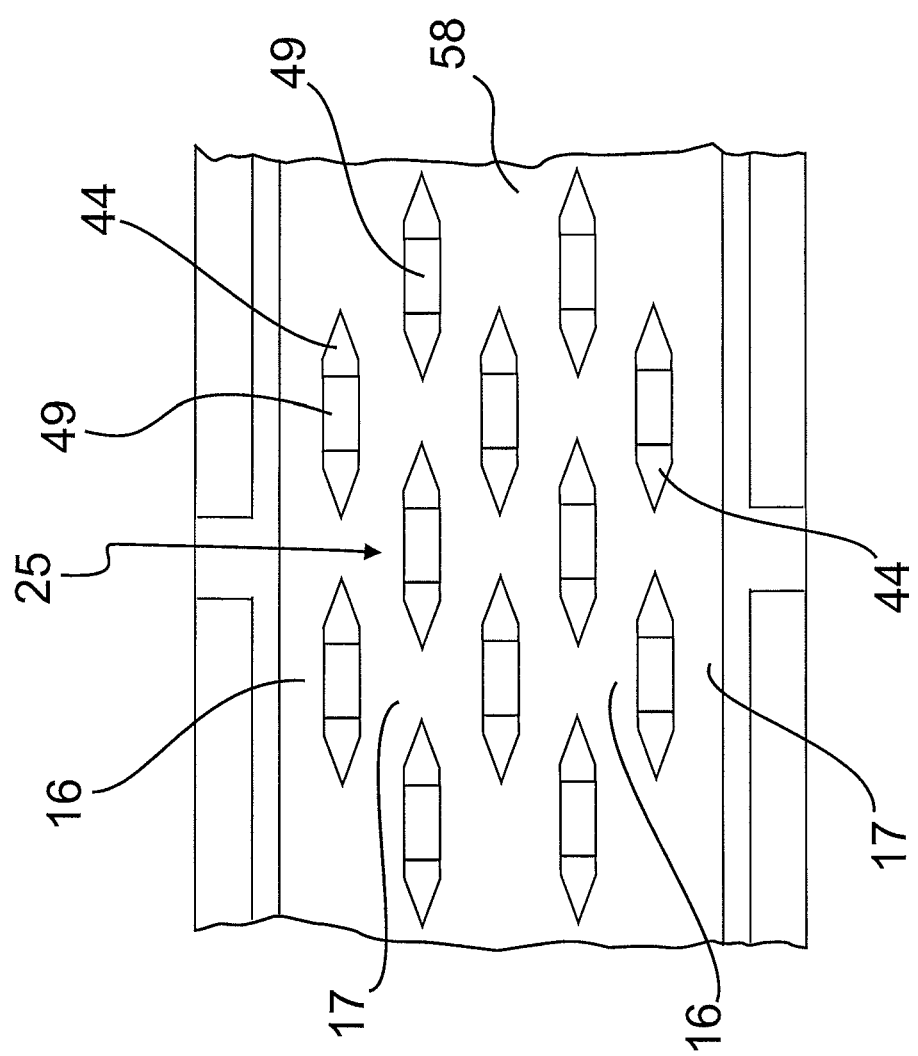
FIG. 13 shows in a depiction as in FIG. 1 a further embodiment of the novel microfluidic system in which the wall structure includes a plurality of partitions.

FIG. 13 shows a further embodiment in which the wall structure 25 has a plurality of partitions 44 each with a slot 49 provided therein. In this microstructure 11, therefore, one microchannel 58 is split into many microchannel segments 16, 17, between each of which a partition 44 runs, otherwise it corresponds to the assembly shown in FIG. 11 where only one microchannel 58 is provided for perfusion.

It is common to all microstructures 11 described insofar that the structure of the inhomogeneous electric field 28 is influenced by the shaping in the region of the aperture 26 and of the slot 49 in order to give preference to different positions for the accumulation of cells depending on the desired cell arrangement to be assembled.

Figure 14:
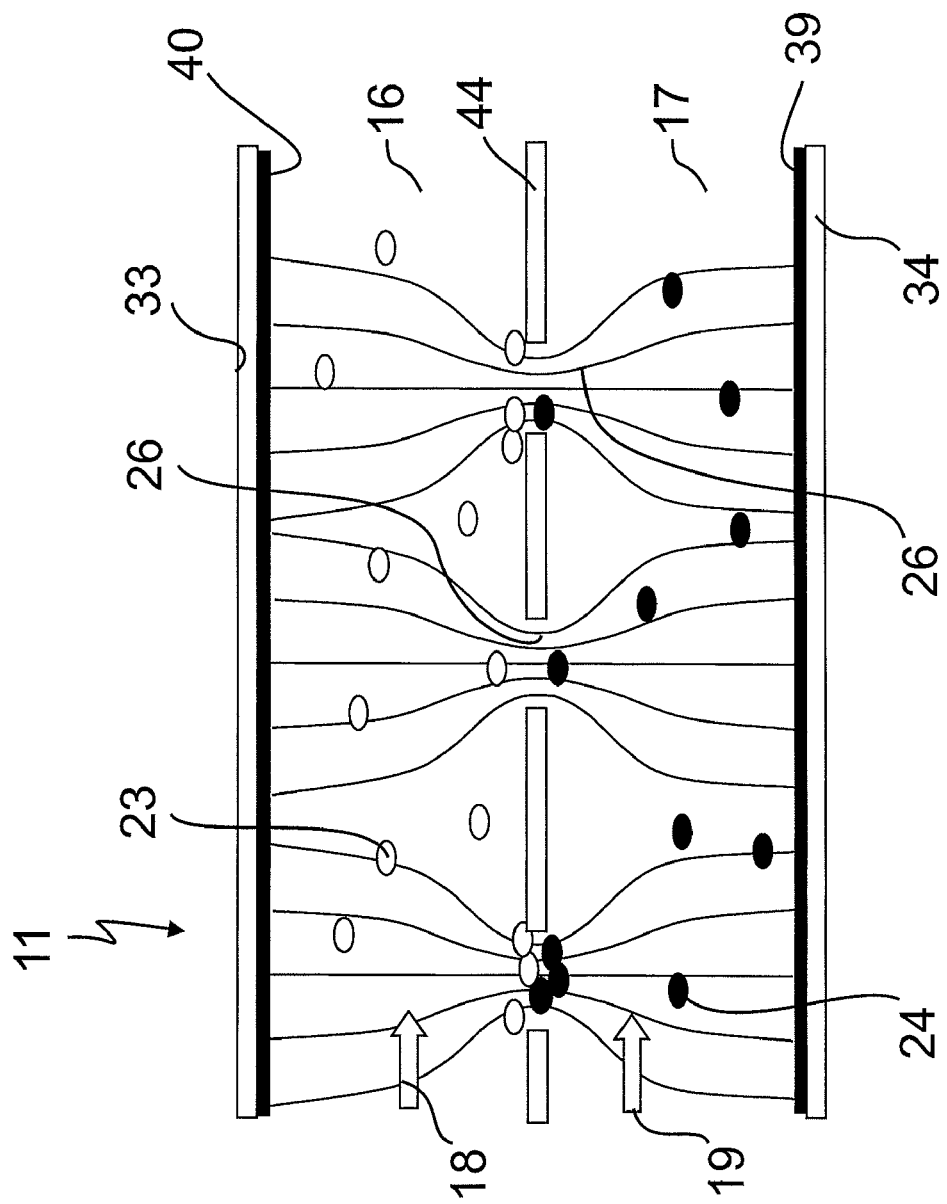
FIG. 14 shows in a depiction as in FIG. 1 a further embodiment of the novel microfluidic system in which a plurality of apertures are provided in the wall structure, cell types different from one another being supplied simultaneously through the two microchannel segments in order to assemble a layered cell arrangement.
Figure 15:
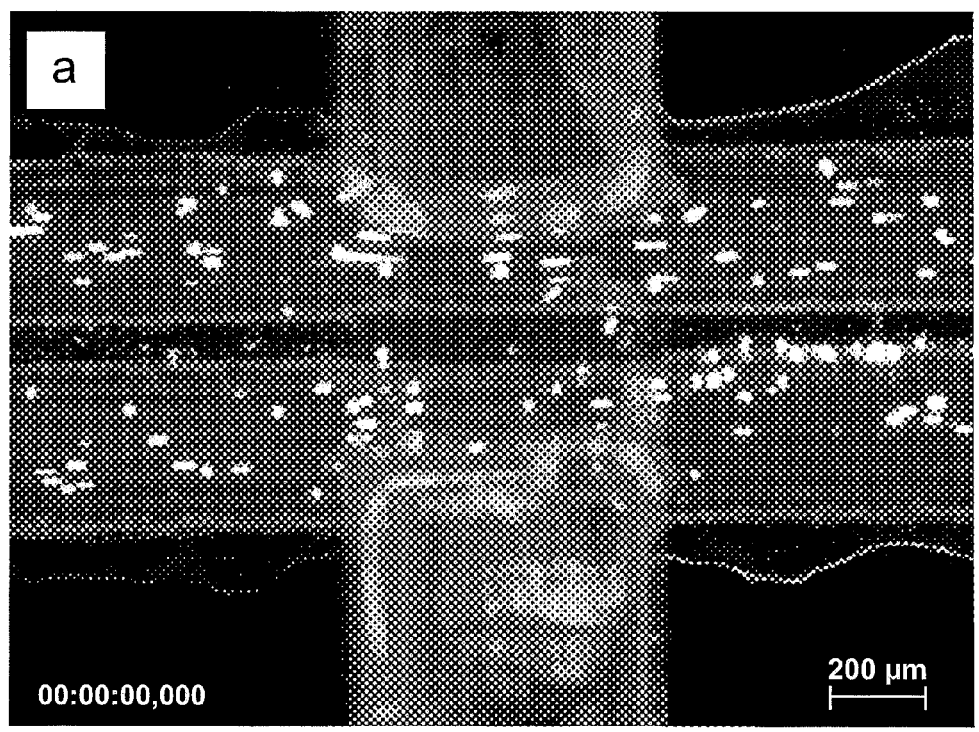
FIGS. 15 to 18 show fluorescence shots of the gradual assembling of aggregates of the LCL 17001 cell line in a microfluidic system which is depicted in principle in the lower part of FIG. 15.
Figure 15:
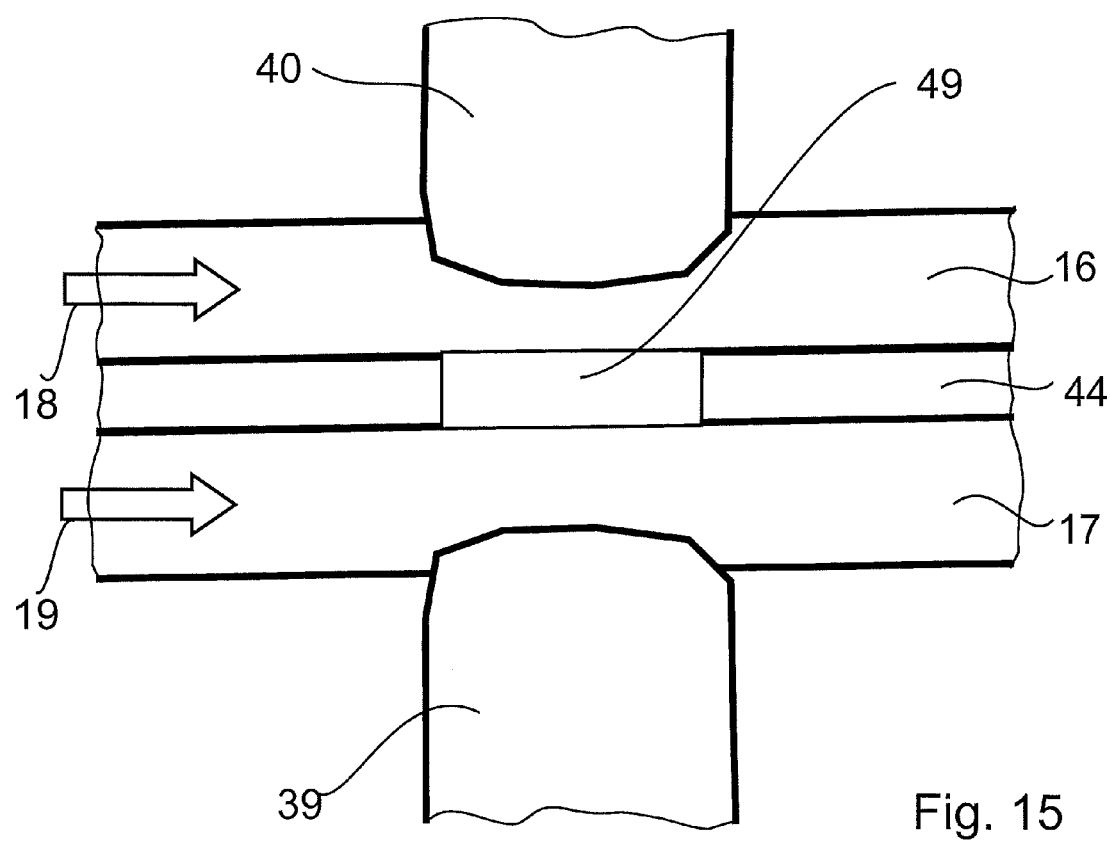
Figure 16:
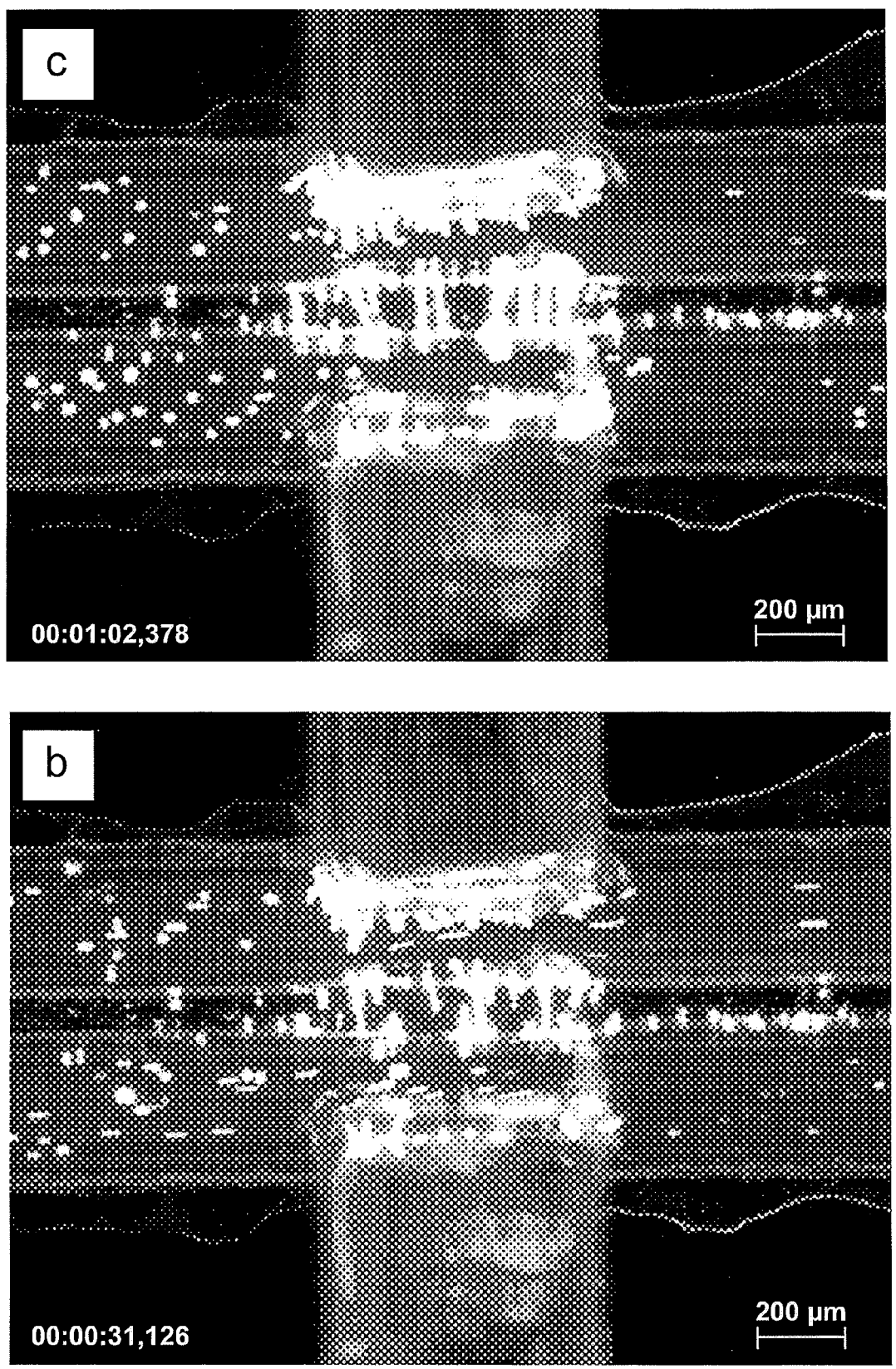
Figure 17:
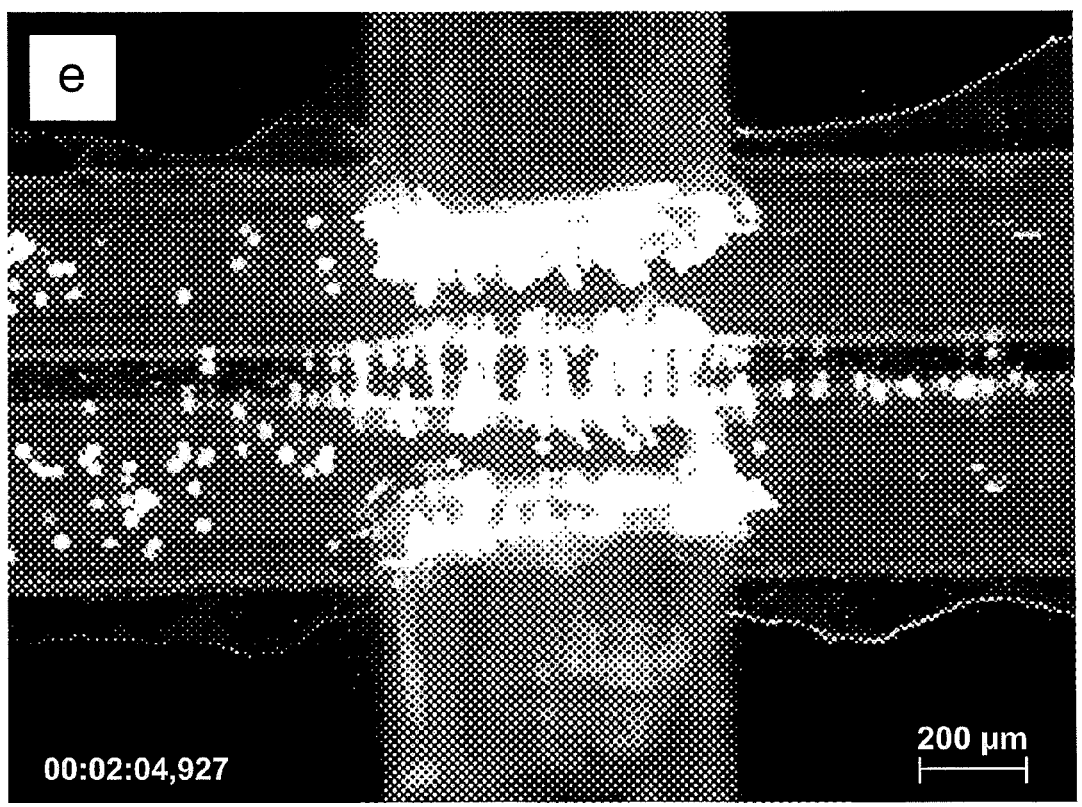
Figure 17:
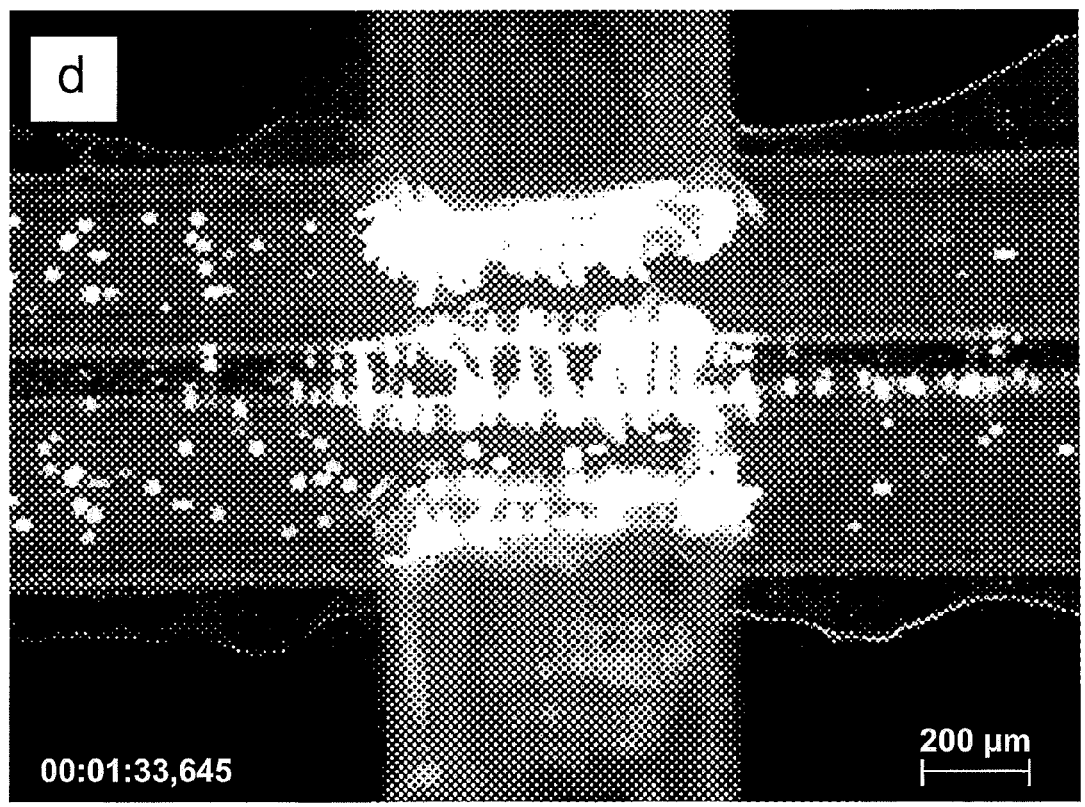
Figure 18:
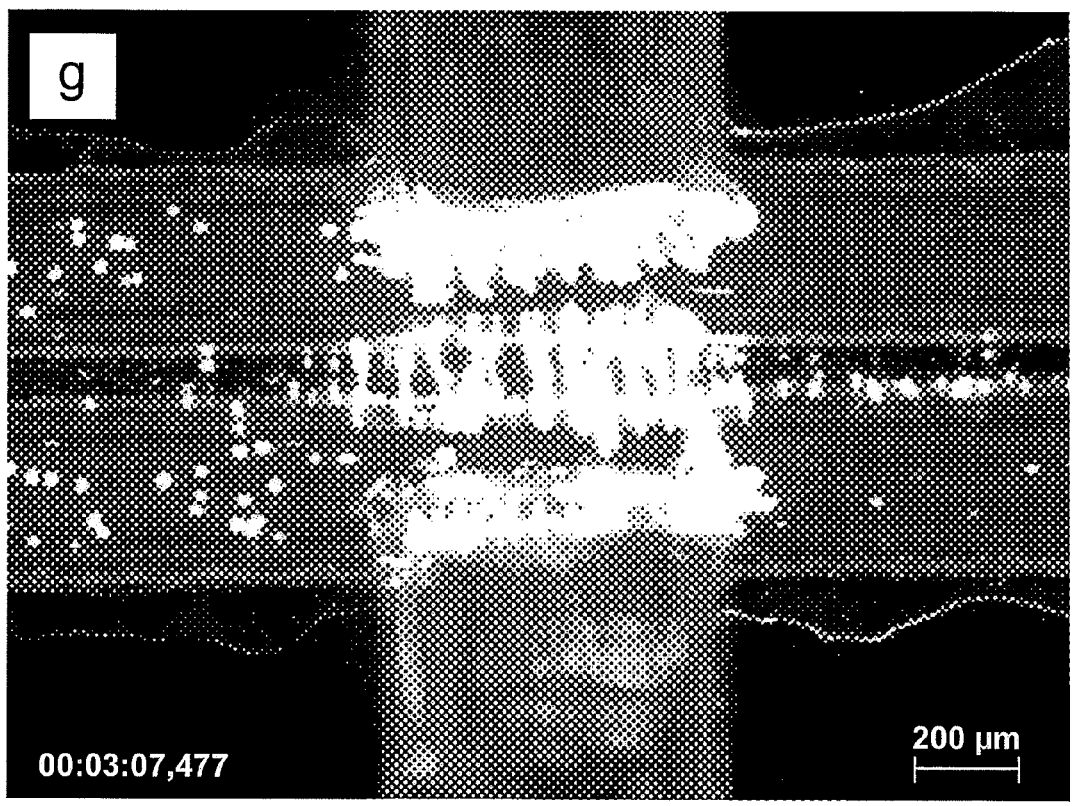
Figure 18:
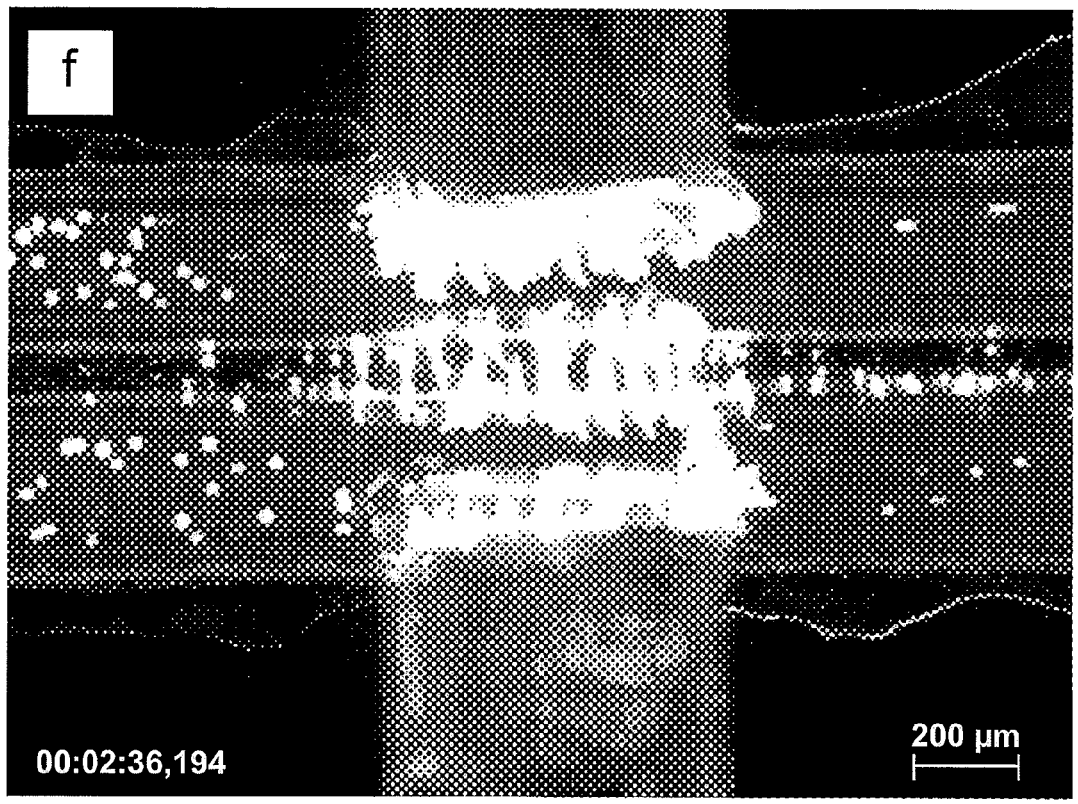

FIG. 14 finally shows as in the depiction in FIGS. 1, 10, 11, 12 and 13 a microstructure 11 in which the microchannel segments 16 and 17 are separated from one another by a partition 44 in which a plurality of apertures 26 are provided that are arranged side by side in the direction of flow 18, 19 and—as not depicted in FIG. 14—also one above another, that is to say parallel to the plane of the drawing. The channel electrodes 38 and 39 extend over the whole region of the partition 44 which is provided with apertures 26.

This structure is suitable for assembling a bilayer layered cell arrangement from cells 23 and 24 which are deposited at the apertures 26 from the two microchannel segments 16 and 17.

As described at the outset, it is possible in this way to simulate the structure of the intestinal epithelium or the blood-brain barrier.

It is then possible for example to supply medium with nutrients and test substances in microchannel segment 16, whereas medium is then transported out of microchannel segment 17 by being able to detect whether the test substances are able to penetrate the membrane formed from cells 23 and 24.

FIGS. 15 to 18 shows by way of example progressing from a to g the assembling of cells in a slot. The structure of the slot 49 is shown in the lower part of FIG. 15; the channel electrodes 39 and 40 are designed to be convex in cross section.

An electric field of frequency 90 kHz and voltage U=54 V pp was applied to the channel electrodes. The fluorescence shots a to g were taken at intervals of about 30 seconds. Progressing from a to g in the fluorescence shots it is evident that increasing numbers of cells, which appear as pale dots, collect in the region of the slot 49.

Cells of the lymphoid cell line of the LCL17001 type were used in the example shown. The media contained cells in a density of $1\times10^6$ per ml of culture medium which comprised 480 mM sucrose in a buffer at about pH 7.0. To analyze the viability, 3 µl of the fluorescent dye Calcein AM were added to 4 ml of the sucrose cell suspension.

The above experiments were carried out in cell culture media for proof of principle experiments using the LCL 17001 cell line.

In the actual experiments, a cell culture medium specific for hepatocytes or the other cell types used in each case is then employed.

Culture medium refers hereinafter in each case to the medium in which the cells grow optimally, whereas suspending medium refers to medium which is optimized to the requirements of the positive dielectrophoresis and which has in particular a low conductivity and ensures the viability of the cells for a relatively short period of a few minutes to hours.

The culture medium used for LCL (lymphoid cell line) is 500 ml of RPMI 1640 culture medium+20% (120 ml) FBS (fetal bovine serum)+6 ml of Penstrep (antibiotics)+2 mmol of L-glutamine; see Lindl, T., *Zell-und Gewebekultur.* 4th edition 2000, Berlin/Heidelberg: Spektrum Akademischer Verlag.

The suspending medium used is DI water+480 mmol of D-sucrose, no buffer correction being carried out because the pH differs from the culture medium by only 0.4, see also Sebastian, A., A.-M. Buckle, and G. H. Markx, "Formation of multilayer aggregates of mammalian cells by dielectrophoresis." *Journal of Micromechanics and Microengineering*, 2006. 16(9): p. 1769.

The assembling and growth behaviour of LCL cells are described in a publication by Nilsson; Nilsson, K., "Human B-lymphoid cell lines" *Hum Cell*, 1992. 5(1): p. 25-41.

The culture medium used for hepatocytes is DMEM (Dulbecco's modified Eagle-Medium)+10% FBS (fetal bovine serum)+0.5 U/ml insulin+7 ng/ml glucagon+20 ng/ml epidermal growth factor+7.5 µg/ml hydrocortisone+100 U/ml penicillin+100 µg/ml streptomycin.

It should also be mentioned concerning the suspending medium used that media with a particularly low conductivity are necessary for positive dielectrophoresis (DEP). These are prepared by reducing the salt and buffer concentration of the culture media as far as possible. Culture media are usually based on a PBS (phosphate buffered saline) solution which contains about 150 mM NaCl, which brings about a conductivity which is too high for positive DEP. To compensate for the reduced osmolarity when the salt is omitted, i.e., in order to avoid bursting of the cells as a result of the concentration difference between cytosol and medium, a sugar, e.g., sucrose or sorbitol is added to the medium instead of the salt in a concentration of up to 500 mM.

The assembly of cells within the novel microfluidic system can also be achieved in an asymmetric microstructure, wherein only the lower part is three-dimensionally patterned, as e.g., in FIGS. 1 to 7, whereby the upper part consists of a planar plate serving as a cover. This greatly facilitates the manufacture of the novel system since no precise alignment of the lower and upper parts is required.

In addition, the lower part may be plane and the upper part be structured. In this case, cells may not sediment into channels where electric field forces may be too low to draw cells into the apertures.

In a further set-up it could be shown that hepatocytes assemble at an electric field frequency of 350 kHz, whereas endothelial cells aggregate at 600 kHz, but dead cells do not aggregate at all.

This is an important finding, as by this the novel system shows a remarkable advantage as compared to conventional assays, since only viable cells are drawn from the medium within the microchannel segments 16, 17 into the apertures 26 and incorporated into the cell assembly.

Further, using these frequencies with the novel system, a liver sinusoid can be aggregated by co-assembly of hepatocytes and endothelial cells as follows:

A mixture of liver cells comprising hepatocytes and endothelial cells are provided through the microfluidic channels. By switching the frequency of the applied voltage to 350 kHz, first only living hepatocytes will be drawn into the aperture, even though both cell types are present in the microchannel segments.

Subsequently, after a sufficient number of living hepatocytes have been assembled in the aperture, which may be measured by increase of electric filed strength, the frequency of the applied voltage is switched to 600 kHz and thereupon living endothelial cells are drawn into the aperture.

Thus, cell types do not have to be separated beforehand and also viability of cells is much less a concern as in conventional culture methods.

Therefore, what is claimed is:

1. A method for assembling and cultivating complex cell arrangements, in which method
   initially a complex cell arrangement is assembled in a microfluidic system for assembling and subsequently cultivating complex cell arrangements, comprising
      a three-dimensional microstructure in which the cell arrangement is assembled and cultivated,
      at least two microchannel segments running in the microstructure and defining a flow direction, through which microchannel segments the microstructure can be perfused from outside with a medium, whereby the microchannel segments run approximately parallel or equidistant to one another at least in sections,
      a wall structure separating the at least two microchannel segments, in which wall structure at least one aperture is provided for connecting the at least two microchannel segments, and
      an electrode arrangement provided at the microstructure in order to generate an inhomogeneous electric field in the region of the at least one aperture, by
   supplying medium with cells for assembling the cell arrangement to the microstructure, and
   generating in the microstructure an inhomogeneous electric field which is determined by the microstructure and which brings about the assembling of a cell arrangement from the supplied cells, and subsequently
   cultivating the cell arrangement assembled in the three-dimensional microstructure by perfusing the three-dimensional microstructure with medium.

2. The method of claim 1, wherein initially first cells for assembling a cell arrangement are supplied to the microstructure through both microchannel segments, and thereafter second cells different from the first cells are supplied in order to assemble a cell arrangement from the second cells on the cell arrangement of the first cells.

3. The method of claim 2, wherein the first cells comprise hepatocytes and the second cells comprise endothelial cells.

4. The method of claim 1, wherein first cells are supplied via the first microchannel segment to the microstructure and, second cells different from the first cells are supplied via the second microchannel segment, to the microstructure.

5. The method of claim 4, wherein the first cells comprise mesenchymal cells and the second cells comprise epithelial cells.

6. The method of claim 4, wherein the first cells comprise astrocytes and the second cells comprise epithelial cells.

7. The method of claim 1, wherein nutrients and/or test substances are supplied to the cell arrangement together with the medium.

8. The method of claim 1, wherein metabolic products are removed from the cell arrangement through a microchannel selected from the group consisting of the two microchannel segments and a further microchannel.

9. A method for investigating complex cell arrangements, in which method
   a cell arrangement is assembled and cultivated by the method of claim 1,
   and the cell arrangement established in this way is investigated on the basis of removed metabolic products.

10. A method for investigating complex cell arrangements, in which method
    a cell arrangement is assembled and cultivated by the method of claim 1,
    and the cell arrangement established in this way is investigated on the basis of markers which are supplied with the medium and which generate a measurable signal in cooperation with the cell arrangement.

* * * * *